(12) United States Patent
Valera et al.

(10) Patent No.: US 6,194,162 B1
(45) Date of Patent: *Feb. 27, 2001

(54) METHOD OF SCREENING FOR COMPOUNDS THAT BIND $P_{2X}$ RECEPTOR

(75) Inventors: Soledad Valera; Gary N Buell, both of Geneva (CH)

(73) Assignee: Glaxo Group Limited, Greenford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/363,745

(22) Filed: Jul. 30, 1999

Related U.S. Application Data

(63) Continuation of application No. 08/750,134, filed as application No. PCT/EP95/01968 on May 24, 1995, now Pat. No. 5,985,603.

(30) Foreign Application Priority Data

May 27, 1994 (GB) .................................................. 9410664
Feb. 9, 1995 (GB) .................................................. 9502480

(51) Int. Cl.[7] ......................... G01N 33/566; A61K 38/00; C12N 15/00
(52) U.S. Cl. ............................ 435/7.2; 435/69.1; 514/2; 514/12; 530/350
(58) Field of Search .................................. 435/7.2, 69.1, 435/325; 530/350; 514/2, 12

(56) References Cited

U.S. PATENT DOCUMENTS 5,985,603 * 11/1999 Valera et al. ........................ 435/69.1

OTHER PUBLICATIONS

Chen, CC et al. A P2X purinoceptor expressed by a subset of sensory neurons. Nature. Oct. 5, 1995; 377(6548):428–431.*

* cited by examiner

Primary Examiner—Prema Mertz
Assistant Examiner—Joseph F. Murphy
(74) Attorney, Agent, or Firm—Nixon & Vanderhye P.C.

(57) ABSTRACT

The $P_{2X}$ receptor of ATP has been cloned and expressed by recombinant DNA technology, so the receptor can be prepared free from other ATP receptors. The $P_{2X}$ receptor enables antibodies to be prepared and is useful in screening compounds for use in a variety of diseases and conditions, including epilepsy, cognition, emesis, pain (especially migraine), asthma, peripheral vascular disease, hypertension, diseases of the immune system, irritable bowel syndrome and premature ejaculation.

6 Claims, 19 Drawing Sheets

Fig. 1A

P2xα 1 cDNA from rat vas deferens

```
  1 gccaaagctgttctgatcacccaggggttttcctcccaacccagaccccaccatcgaacctccaactctgtcccacct                                                              80
 81 agcctgctcctgtccttaagggccgggaagccccagtcactccactgctattgtagatgcagatgtggcctgccctga                                                             160
161 ccatagaggccgtgtgggggtgttcatctctgagccccttctgcccacc ATG GCT CGG CGG CTG CAA GAT                                                              230
  1                                                    M   A   R   R   L   Q   D                                                                7
231 GAG CTG TCA GCC TTC TTC TTT GAA TAT GAC ACT CCC CGG ATG GTG CTG GTA CGA AAC AAG                                                             290
  8  E   L   S   A   F   F   F   E   Y   D   T   P   R   M   V   L   V   R   N   K                                                             27
291 AAG GTG GGA GTC ATT TTC CGT CTG ATC CAG TTG GTG GTT CTG GTC TAC GTC ATT GGG TGG                                                             350
 28  K   V   G   V   I   F   R   L   I   Q   L   V   V   L   V   Y   V   I   G   W                                                             47
351 GTG TTT GTC TAT GAA AAA GGA TAC CAG ACC TCA AGT GAC CTC ATC AGC AGT GTG TCC GTG                                                             410
 48  V   F   V   Y   E   K   G   Y   Q   T   S   S   D   L   I   S   S   V   S   V                                                             67
411 AAG CTC AAG GGC TTG GCT GTG ACC CAG CTC CAG GGC CTG GGA CCC CAG GTC TGG GAC GTG                                                             470
 68  K   L   K   G   L   A   V   T   Q   L   Q   G   L   G   P   Q   V   W   D   V                                                             87
471 GCT GAC TAT GTC TTC CCA GCA CAC GGG GAC AGC TCC TTT GTA GTT ATG ACC AAC TTC ATC                                                             530
 88  A   D   Y   V   F   P   A   H   G   D   S   S   F   V   V   M   T   N   F   I                                                            107
531 GTG ACC CCT CAG CAG ACT CAA GGC CAT TGT GCA GAG AAC CCA GAA GGT GGC ATA TGC CAG                                                             590
108  V   T   P   Q   Q   T   Q   G   H   C   A   E   N   P   E   G   G   I   C   Q                                                            127
```

Fig. 1B

```
591  GAT GAC AGT GGC TGC ACT CCA GGA AAA GCA GAA AGG AAA GCC CAA GGT ATT CGC ACA GGC  650
128  D   D   S   G   C   T   P   G   K   A   E   R   K   A   Q   G   I   R   T   G   147

651  AAC TGT GTG CCC TTC AAT GGC ACT GTG AAG ACA TGT GAG ATC TTT GGT TGT CCT GTA      710
148  N   C   V   P   F   N   G   T   V   K   T   C   E   I   F   G   C   P   V       167

711  GAG GTG GAT GAC AAG ATC CCA AGC CCT GCT CTT CGT GAG GCT GAG AAC TTC ACC CTC      770
168  E   V   D   D   K   I   P   S   P   A   L   R   E   A   E   N   F   T   L       187

CCC CAG CTG GCA CAT GGC TGC TAC CCA TGC CCT CCA CAC AG     sequence of RP-2
     P   Q   L   A   H   G   C   Y   P   C   P   P   H   R 771  TTC ATC AAA AAC AGC ATC AGC TTT CCA AGG TTC AAG GTC AAC CGC AAC CTG GTA GAG      830
188  F   I   K   N   S   I   S   F   P   R   F   K   V   N   R   N   L   V   E       207

831  GAG GTG AAC GGC ACC TAC ATG AAG AAG TGC CTC TAT CAC AAG ATT CAA CAC CCC CTG TGC  890
208  E   V   N   G   T   Y   M   K   K   C   L   Y   H   K   I   Q   H   P   L   C   227

891  CCA GTC TTC AAC CTT GGC TAT GTG GTG CGA GAG TCA GGC CAG GAC TTC CGC AGC CTT GCT  950
228  P   V   F   N   L   G   Y   V   V   R   E   S   G   Q   D   F   R   S   L   A   247

951  GAG AAG GGT GGG GTG GTT GGT ATC ACC ATT GAC TGG AAG TGT GAT CTG GAC TGG CAC GTT  1010
248  E   K   G   G   V   V   G   I   T   I   D   W   K   C   D   L   D   W   H   V   267

1011 CGG CAC TGC AAA CCC ATC TAC CAG TTC CAC GGA CTG TAT GGG GAG AAG AAC CTG TCT CCA  1070
268  R   H   C   K   P   I   Y   Q   F   H   G   L   Y   G   E   K   N   L   S   P   287
```

Fig. 1C

```
1071 GGC TTC AAC TTC AGA TTT GCC AGG CAT TTC GTG CAG AAT GGG ACA AAC CGT CGT CAC CTC 1130
 288  G   F   N   F   R   F   A   R   H   F   V   Q   N   G   T   N   R   R   H   L  307

1131 TTC AAG GTG TTT GGG ATT CAC TTT GAT ATC CTT GTG GAT GGC AAG GCT GGG AAG TTT GAC 1190
 308  F   K   V   F   G   I   H   F   D   I   L   V   D   G   K   A   G   K   F   D  327

1191 ATC ATC CCT ACT ATG ACT ATC GGT TCT GGG ATT GGC ATC TTT GGA GTG GCC ACA GTG 1250
 328  I   I   P   T   M   T   I   G   S   G   I   G   I   F   G   V   A   T   V  347

1251 CTT TGT GAT CTC TTA TTG CTC ATC CAC ATC CTG CCT AAG AGG CAC TAC TAC AAG CAG AAG AAG 1310
 348  L   C   D   L   L   L   L   I   H   I   L   P   K   R   H   Y   Y   K   Q   K   K  367

1311 TTC AAA TAT GCC GAG GAC ATG GGG CCG GGA GAG GGT GAA CAT GAC CCC GTG GCC ACC AGC 1370
 368  F   K   Y   A   E   D   M   G   P   G   E   G   E   H   D   P   V   A   T   S  387

1371 TCC ACT CTG GGC CTG CAG GAG AAC ATG AGG ACC TCC TGA ccttagtcttgagatccggacttgacgc 1437
 388  S   T   L   G   L   Q   E   N   M   R   T   S   *                                400

1438 agtgtgtggcttccgcaagggctgatggcttgagccaggcagagggcattcccagaggcttcctgcaaggcagaca 1517

1518 ccagtggccctctgttcagcatgaagacaggcaagactttggattcagagctctgttcagttccacatgtcccctc 1597 end of rp-2 sequence -/

1598 ctgagggatgcctcctccagtttccaccaattgggttcatatggctggccctcacacatctatactctagcttgtg 1677

1678 cttaaggctcaggctgcattgtctttcccacagcctaccgctccatgattggctcttccacatgtcctcctagcc 1757

1758 agatgtgtcagtttgaactttaattaaatataataaaaaaaaaaaaaaaaaaaaaaaaaaaaa 1837
```

Fig. 2A rat P2X clone 3

```
  1  cgcagcgagcctgccgagctggtggtgagctacgaccgacctggcgaggggacccacagtgtccaaggc          80

81  gcggacggtcggcggagcc ATG GCG CCG CGC ATC GTG CTC ATC CGC AGC CGT AAA GTG GGG CTC ATG AAC CGC GCG GTG TTC GAG TAC     145
                          M   A   P   R   I   V   L   I   R   S   R   K   V   G   L   M   N   R   A   V   F   E   Y     15

146  GAC ACG CCG CGC ATC CTG GCT TAC ATC GTC GGG TGG GTG TTC GTG TGG GAA AAG GGC TAC CAG                                  205
      D   T   P   R   I   L   A   Y   I   V   G   W   V   F   V   W   E   K   G   Y   Q                                  35

206  CAG CTG CTC ATC TCC CTG GTC AGC TCG GTC ACA ACC AAA GCC AAA GGT GTG GCT GTG ACC AAC                                  265
      Q   L   L   I   S   L   V   S   S   V   T   T   K   A   K   G   V   A   V   T   N                                  55

266  GAA ACG GAC ACC CAC AGC AGT GGA GTT GCG ACT GGA AGA TGT GTT CCT TTC AAT GAG TCT                                      325
      E   T   D   T   H   S   S   G   V   A   T   G   R   C   V   P   F   N   E   S                                      75

326  ACC TCT CAG CTT GGA TTC CGG ATC TGG GAC GTG GCG GAC TAT GTG ATT CCA GCT CAG GAG                                      385
      T   S   Q   L   G   F   R   I   W   D   V   A   D   Y   V   I   P   A   Q   E                                      95

386  GAA AAC TCC CTC TTC ATT ATG ACC AAC ATG ATT GTC ACC GTG AAC CAG ACA CAG AGC ACC                                      445
      E   N   S   L   F   I   M   T   N   M   I   V   T   V   N   Q   T   Q   S   T                                     115

446  TGT CCA GAG ATT CCT GAT AAG ACC AGC ATT TGT AAT TCA GAC GCC GAC TGC ACT CCT GGC                                      505
      C   P   E   I   P   D   K   T   S   I   C   N   S   D   A   D   C   T   P   G                                     135

506  TCC GTG GAC ACC CAC AGC AGT GGA GTT GCT GCG ACT GGA AGA TGT GTT CCT TTC AAT GAG TCT                                  565
      S   V   D   T   H   S   S   G   V   A   T   G   R   C   V   P   F   N   E   S                                     155

566  GTG AAG ACC TGT GAG GTG GCT GCA TGG TGC CCG GTG GAG AAC GAC GTT GGC GTG CCA ACG                                      625
      V   K   T   C   E   V   A   A   W   C   P   V   E   N   D   V   G   V   P   T                                     175

626  CCG GCT TTC TTA AAG GCT GCA GAA AAC TTC ACC CTC TTG GTA AAG AAC AAC ATC TGG TAC                                      685
      P   A   F   L   K   A   A   E   N   F   T   L   L   V   K   N   N   I   W   Y                                     195
```

Fig. 2B

```
 686 CCC AAG TTT AAC TTC AGC AAG AGG AAC ATC CTC CCC AAC ATC ACC ACG TCC CTC AAA  745
 196  P   K   F   N   F   S   K   R   N   I   L   P   N   I   T   T   S   Y   L   K   215

746 TCG TGC ATT TAC AAT GCT CAA ACG GAT CCC TTC TGC CCC ATA TTC CGT CTT GGC ACA ATC  805
 216  S   C   I   Y   N   A   Q   T   D   P   F   C   P   I   F   R   L   G   T   I   235

806 GTG GGG GAC GCG GGA CAT AGC TTC CAG GAG ATG GCA GTT GAG GGA GGC ATC ATG GGT ATC  865
 236  V   G   D   A   G   H   S   F   Q   E   M   A   V   E   G   G   I   M   G   I   255

866 CAG ATC AAG TGG GAC TGC AAC CTG GAT AGA GCC GCC TCC CTT TGC CTG CCC AGA TAT TCC  925
 256  Q   I   K   W   D   C   N   L   D   R   A   A   S   L   C   L   P   R   Y   S   275

926 TTC CGG CGC CTG GAC ACC CGG GAC CTG GAA CAC AAT GTG TCT CCT GGC TAC AAT TTC AGG  985
 276  F   R   R   L   D   T   R   D   L   E   H   N   V   S   P   G   Y   N   F   R   295

986 TTT GCC AAG TAC TAC AGG GAC CTG GCC GGC AAA GAG CAG CGC ACA CTC ACC AAG GCG TAC 1045
 296  F   A   K   Y   Y   R   D   L   A   G   K   E   Q   R   T   L   T   K   A   Y   315

1046 GGC ATC CGC TTT GAC ATC ATC GTG TTT GGA AAG GCT GGG GTG CTC CTC TGT GAC ATC CCT ACC 1105
 316  G   I   R   F   D   I   I   V   F   G   K   A   G   V   L   L   C   D   I   P   T   335

1106 ATG ATC AAC GTT GGC TCT TGG CTT GCG CTC CTC TAC TAC AAA TAC AAG TAT GTG 1165
 336  M   I   N   V   G   S   W   L   A   L   L   Y   Y   K   Y   K   Y   V   355

1166 ATA GTC CTC TAC TGC ATG AAG AAA TAC CGG GAC GTG CTC TGT GAC GTC 1225
 356  I   V   L   Y   C   M   K   K   Y   R   D   V   L   C   D   V   375

1226 GAA GAC TAC GAG CAG GGT CTT TCG GGG GAG ATG AAC CAG TGA cgcctaagttacattccacccc 1291
 376  E   D   Y   E   Q   G   L   S   G   E   M   N   Q   *                              389
```

Fig. 2C

```
1292  gctcagcccgcgaagcagaaagatggggagagatggctactgctctgtcactctagagaagctccagagtttcagctc  1371
1372  agtcctccactccacaaatactccaggttgccaagcacatccttgttggagcccggctcttgctctgtcctcagatgggc  1451
1452  ttccagatacaagaatcctcctgcttctgcctctctaggaatgctggatcaaacatgtcactgcaatgccattcccat  1531
1532  ggggagttggcatttttacattttacccttcccttttgtatacatctaaggctgccctcagacgcaagacgtcttcc  1611
1612  acccctatacaccctttaatctccactgtgtgtgggaggggggtcgtttgcacacgacgacgtggatgtctggtgct  1691
1692  gttggctgggccacctgtggcttatacagtgtgagcgtgagctaggaggtaggaagggtctgagagcagacactgctggc  1771
1772  ttacggacaggccaggctctgtccacgcacctttattctcaaggaaggaggctctctcaggtgctgtcagcaggcctggg  1851
1852  acaccattcctctcccctataatcagagaagtgtccctgtagcaaaggcagggttagctttttccttttataaggctgt  1931
1932  gttgaaatgacctaggaccaaacattaaaagaataatttttaaaaaaaaaaaaaaaaa  1997
```

Fig. 3A rat P2X clone 6

```
  1 cactgggctacagtgctggcttacaggaactggctcttttcctcaagcctcattaagcagccactccagttcttgat    80
 81 ctttgtctcccagtcctgaagtcctttctcctcctaggctgcatccacagccctttctaagtgctgtgagcagttcctca  160
161 gt ATG AAC TGT ATA TCA GAC TTC TTC ACC TAC GAG ACT ACC AAG TCG GTG GTT GTG AAG  219
  1    M   N   C   I   S   D   F   F   T   Y   E   T   T   K   S   V   V   V   K   19
220 AGC TGG ACC ATT GGG ATC ATC AAC CGA GCC GTC CAG CTG CTG ATT ATC TCC TAC TTT GTG  279
 20   S   W   T   I   G   I   I   N   R   A   V   Q   L   L   I   I   S   Y   F   V   39
280 GGG TGG GTT TTC TTG CAT GAG AAG GCC TAC CAA GTG AGG GAC ACC GCC ATT GAG TCC TCA  339
 40   G   W   V   F   L   H   E   K   A   Y   Q   V   R   D   T   A   I   E   S   S   59
340 GTA GTT ACA AAG GTG ACA AAG GGC TTT GGG CGC TAT GCC AAC AGA GTC ATG GAC GTG TCG GAT  399
 60   V   V   T   K   V   T   K   G   F   G   R   Y   A   N   R   V   M   D   V   S   D   79
400 TAT GTG ACC CCA CCC CAG GGC ACC TCT GTC TTT GTC ATC ATC ACC AAA ATG ATC GTT ACT  459
 80   Y   V   T   P   P   Q   G   T   S   V   F   V   I   I   T   K   M   I   V   T   99
460 GAA AAT CAA ATG CAA GGA TTC TGT CCA GAG AAT GAA GAG AAG TAC CGC TGT GTG TCT GAC  519
100   E   N   Q   M   Q   G   F   C   P   E   N   E   E   K   Y   R   C   V   S   D  119
520 AGC CAG TGT GGG CCT GAA CGC TTC CCA GGT GGG GGG ATC CTC ACC GGC CGC TGC GTG AAC  579
120   S   Q   C   G   P   E   R   F   P   G   G   G   I   L   T   G   R   C   V   N  139
```

Fig. 3B

```
 580 TAC AGC TCT GTT CTC CGG ACC TGT GAG ATC CAG GGC TGG TGC CCC ACT GAG GTG GAC ACC  639
 140  Y   S   S   V   L   R   T   C   E   I   Q   G   W   C   P   T   E   V   D   T   159

640 GTG GAG ATG CCT ATC ATG ATG GAG GCT GAG AAC TTC ACC ATT TTC ATC AAG AAC AGC ATC  699
 160  V   E   M   P   I   M   M   E   A   E   N   F   T   I   F   I   K   N   S   I   179

700 CGT TTC CCT CTC TTC AAC TTT GAG AAG GGA AAC CTC CTG CCT AAC CTC ACC GAC AAG GAC  759
 180  R   F   P   L   F   N   F   E   K   G   N   L   L   P   N   L   T   D   K   D   199

760 ATA AAG AGG TGC CGC TTC CAC CAC CCT GAA AAG GCC CCA TTT TGC AAG CTG AGG GTA GGG  819
 200  I   K   R   C   R   F   H   H   P   E   K   A   P   F   C   K   L   R   V   G   219

820 GAT GTG GTT AAG TTT GCT GGA CAG GAT TTT GCC AAG CTA AGG ACG GGT GGC GTT CTG  879
 220  D   V   V   K   F   A   G   Q   D   F   A   K   L   A   R   T   G   G   V   L   239

880 GGT ATT AAG ATC GGC TGG GTG TGC GAT CTA GAC AAG GCC TGG GAC CAG TGC ATC CCT AAA  939
 240  G   I   K   I   G   W   V   C   D   L   D   K   A   W   D   Q   C   I   P   K   259

940 TAT TCC TTC ACT CGG CTG GAT GGA GTT TCT GAG AAA AGC AGT GTT TCC CCT GGC TAC AAC  999
 260  Y   S   F   T   R   L   D   G   V   S   E   K   S   S   V   S   P   G   Y   N   279

1000 GGC GAG TAC AGC GAG TAC CGC ACA CTC CTG AAG 1059
 280  G   E   Y   S   E   Y   R   T   L   L   K   299

1060 GCT TTT GGC ATC CGC TTT GAT GTG CTG GTA TAT GGG AAC GCT GGC AAG TTC AAC ATC ATC 1119
 300  A   F   G   I   R   F   D   V   L   V   Y   G   N   A   G   K   F   N   I   I   319
```

Fig. 3C

```
1120 CCC ACC ATT ATC AGC TCG GTG GCG GCC TTC ACT TCT GTG GGA GTG GGC ACT GTT CTC TGT 1179
 320  P   T   I   I   S   S   V   A   A   F   T   S   V   G   V   G   T   V   L   C  339
1180 GAC ATC ATC CTG CTC AAT TTC CTC AAA GGG GCT GAT CAC TAC AAA GCC AGG AAG TTT GAG 1239
 340  D   I   I   L   L   N   F   L   K   G   A   D   H   Y   K   A   R   K   F   E  359
1240 GAG GTG ACT GAG ACA ACA CTG AAG GGT ACT GCG TCA ACC AAC CCA GTG TTC GCC AGT GAC 1299
 360  E   V   T   E   T   T   L   K   G   T   A   S   T   N   P   V   F   A   S   D  379
1300 CAG GCC ACT GTG GAG AAG CAG TCT ACA GAC TCA GGG GCC TAT TCT ATT GGT CAC tagggcct 1361
 380  Q   A   T   V   E   K   Q   S   T   D   S   G   A   Y   S   I   G   H           397
1362 cttcccagggttccatgctccaccctaggctgcaaacaggccactccactctatctaagcagtcaggggtggggagg 1441
1442 gggagaagaagggctgctatttctgctgttcaccccaaagactagatccagatatctaggccctccactgttcaacagata 1521
1522 ggcaatgcttcccactaagacttgaatccttgcctttaccccctgcatgcctccccacctgcttccctgatcccaggacag 1601
1602 cagcatccaccccttccaaaggattgagaaatggtagctaaggttacacccatagaaccatagaccaccgtaccacgtaccaagcactt 1681
1682 ccacacacatattatccctttcaccctaaaataatccctataaggtagaaaaaaaaaaaaaaaaaaaa 1753
```

Fig. 4A

```
1    gcctccagctgacctctggctcctgtcctctgctccacctgaccgccctgctcctcctaaggggcaggaagcccca    80

81   gaagctctaccatcgacgtgtggtggtggcaccggctcaccctgagagagagaggggtgcaggggctcagttctgagcc  160

161  cagccggccacc ATG GCA CGG CGG TTC CAG GAG GAG CTG GCC GCC TTC CTC TTC GAG TAT      221
                 M   A   R   R   F   Q   E   E   L   A   A   F   L   F   E   Y        16

222  GAC ACC CCC ATG GTG CTG GTG CGT AAT AAG AAG GTG GGC GTT ATC TTC CGA CTG ATC      281
     D   T   P   M   V   L   V   R   N   K   K   V   G   V   I   F   R   L   I        36

282  CAG CTG GTG CTG GTC TAC GTC ATC GGG TGG GTG TTT CTC TAT GAG AAG GGC TAC CAG      341
     Q   L   V   L   V   Y   V   I   G   W   V   F   L   Y   E   K   G   Y   Q        56

342  ACC TCG AGC GGC CTC ATC AGC AGT GTC TCT GTG AAA CTC AAG GGC CTG GCC GTG ACC      401
     T   S   S   G   L   I   S   S   V   S   V   K   L   K   G   L   A   V   T        76

402  CTC CCT GGC CTC TTC GTG CCC CAG GTC TGG GAT GTG GCT GAC TAC GTC TTC CCA GCC      461
     L   P   G   L   F   V   P   Q   V   W   D   V   A   D   Y   V   F   P   A        96

462  GAC AAC TCC TTC GTG ATG ACC AAT TTC ATC GTG ACC CCG AAG CAG ACT CAA GGC TAC      521
     D   N   S   F   V   M   T   N   F   I   V   T   P   K   Q   T   Q   G   Y        116

522  TGC GCA GAG CAC CCA GAA GGG GGC ATA TGC AAG GAA GAC AGT GGC TGT ACC CCT GGG AAG  581
     C   A   E   H   P   E   G   G   I   C   K   E   D   S   G   C   T   P   G   K    136
```

Fig. 4B

```
582  GCC AAG AGG AAG GCC CAA GGC ATC CGC ACG GGC AAG TGT GTG GCC TTC AAC GAC ACT GTG  641
137   A   K   R   K   A   Q   G   I   R   T   G   K   C   V   A   F   N   D   T   V   156

642  AAG ACG TGT GAG ATC TTT GGC TGG TGC CCC GTG GAG GTG GAT GAC ATC CCG CGC CCT       701
157   K   T   C   E   I   F   G   W   C   P   V   E   V   D   D   I   P   R   P       176

702  GCC CTT CTC CGA GAG GCC GAG AAC TTC ACT CTT TTC ATC AAG AAC AGC ATC AGC TTT CCA  761
177   A   L   L   R   E   A   E   N   F   T   L   F   I   K   N   S   I   S   F   P   196

762  CGC TTC AAG GTC AAC AGG CGC AAC CTG GTG GAG GAG AAT GCT GCC CAC ATG AAG ACC      821
197   R   F   K   V   N   R   R   N   L   V   E   E   N   A   A   H   M   K   T       216

822  TGC CTC TTT CAC AAG ACC CTG CAC CCC CTG TGC CCA GTC TTC CAG CTT GGC TAC GTG GTG  881
217   C   L   F   H   K   T   L   H   P   L   C   P   V   F   Q   L   G   Y   V   V   236

882  CAA GAG TCA GGC CAG AAC TTC AGC ACC CTG GCT GAG AAG GGT GGA GTG GTT GGC ATC ACC  941
237   Q   E   S   G   Q   N   F   S   T   L   A   E   K   G   G   V   V   G   I   T   256

942  ATC GAC TGG CAC TGT GAC CTG GAC AAA AAT CTC TCC CCA GGC CAC TGC AGA CCC ATC TAT GAG TTC 1001
257   I   D   W   H   C   D   L   D   K   N   L   S   P   G   H   C   R   P   I   Y   E   F   276

1002 CAT GGG CTG TAC GAA GAG AAA AAT CTC TCC CCA GGC TTC AAC TTC AGG TTT GCC AGG CAC  1061
277   H   G   L   Y   E   E   K   N   L   S   P   G   F   N   F   R   F   A   R   H   296

1062 TTT GTG GAG AAC GGG ACC AAC TAC CGT CAC CTC TTC AAG GTG TTT GGG ATT CGC TTT GAC  1121
297   F   V   E   N   G   T   N   Y   R   H   L   F   K   V   F   G   I   R   F   D   316
```

Fig. 4C

```
1122 ATC CTG GTG GAC GGC AAG GCC GGG AAG TTT GAC ATC ATC CCT ACA ATG ACC ACC ATC GGC  1181
 317  I   L   V   D   G   K   A   G   K   F   D   I   I   P   T   M   T   T   I   G   336

1182 TCT GGA ATT GGC ATC TTT GGG GTG GCC ACA GTT CTC TGT GAC CTG CTG CTT CAC ATC       1241
 337  S   G   I   G   I   F   G   V   A   T   V   L   C   D   L   L   L   H   I        356

1242 CTG CCT AAG AGG CAC TAC TAC AAG CAG AAG TTC AAA TAC GCT GAG GAC ATG GGG CCA       1301
 357  L   P   K   R   H   Y   Y   K   Q   K   F   K   Y   A   E   D   M   G   P        376

1302 GGG GCG GCT GAG CGT GAC CTC GCA GCT ACC AGC TCC ACC CTG GGC CAG GAG AAC ATG       1361
 377  G   A   A   E   R   D   L   A   A   T   S   S   T   L   G   Q   E   N   M        396

1362 AGG ACA TCC TGA tgctcggcccaactcctgactggtgtgagcttcagcctggagcctggagcccctggtgggtcc  1437
 397  R   T   S   *                                                                   400

1438 cagccagggcagagggcctcccccaggaagtctctcctcagccaggcagagagcagttgccagaagctcaggt         1517
1518 gcatagtaggagagacctgtgcaaatctgagctcccggctcccacacaccctgagggaggcctaccctagcctcag      1597
1598 ccgctcctgtggggaatggctgggggtttgggcaggacccctccacacactgtcacccctagcttcctgtgttctctctcc  1677
1678 ggactctcattatccaacccgctgctcctccattctctagatctgtgctcctccgatgtggcagtaacatagggtgac    1757
1758 taaattaaactaaaaataaatagaatgaaacacaaaattcaattccctggctgaactagccacattcaactgctcagta  1837
```

*Fig. 4D*

```
1838  gatacgtgtggttagtggctgccatactggacagctcggggcattttcactgtcaaagaagttctattagacagccctg  1917
1918  cttgagccctgtttcttcctggcttcggttccctggggaacttatcgacaatgcaagctcctggcccaccccagacc    1997
1998  tcctgaaccaaaagctccagggctggccgtatgatctgtgtggatggcaaactcccaggccattctggacctaagttt  2077
2078  aagaagtgccgtcctgaactttctgactctaagctcctgagcgggagtcagacttagccctgagcctgcacttcctgtt  2157
2158  caggtgcagacactgaacaggtctcaaacacccttcagcatgtgtgttgctcacgtgccacacagtgtctcatgca    2237
2238  cacaacccagtgtacacacaccactacgtgcacacagcatcctccacactgtatgtgaacagcttggccctgcaaac   2317
2318  acaaccatctacacacacatctacacccccaagcacacacacatgtccgtgccatgtcacctccatagtcacctcc   2397
2398  tccaagtgtgccaggccaggacagccctccctgccctgaatcctactcagctacctcggttgggtgggagcccagc    2477
2478  caaatcctggctccctgcctgtgtcagcccccagctcccaaggcctgcctgctctgtctgaacagaaggtctgggg   2557
2558  aagcgagggggtggagtacaataaaggaatgaggacaaacaaaaaaaaaaaaaaaaaaaa                   2637
2638  aaaaaa                                                                           2643
```

Fig. 5

```
                  TM-1
Human MARRFQELAAFLFEYDTPRMVLVRNKKVGVIFRLIQLVVLVYVIGWVFL    50
Rat   MARRLQELSAFFFEYDTPRMVLVRNKKVGVIFRLIQLVVLVYVIGWVFV Human YEKGYQTSSGLISSVSVKLKGLAVTQLEGLGPQVWDVADYVFPAQGDNSF   100
Rat   YEKGYQTSSDLISSVSVKLKGLAVTQLQGLGPQVWDVADYVFPAHGDSSF Human VVMTNFIVTFKQTQGYCAEHPEGGICKEDSGCTPGKAKRKAQGIRTGKCV   150
Rat   VVMTNFIVTFQQTQGHCAENPEGGICQDDSGCTPGKAERKAQGIRTGNCV Human AFNDTVKTCEIFGWCPVEVDDIPRPALLREAENFTLFIKNSISFPRFKV    200
Rat   EFNGTVKTCEIFGWCPVEVDDKIFSPALLREAENFTLFIKNSISFPRFKV Human NRRNLVEEVNAAHMKTCLFHKTLHPLCPVFQLGYVVQESGQNFSTLAEKG   250
Rat   NRRNLVEEVNGTYMKKCLYHKIQHPLCPVFNLGYVVRESGQDFRSLAEKG Human GVVGITIDWHCDLDWHVRHCRPIYEFHGLYEEKNLSPGFNFRFARHFVEN   300
Rat   GVVGITIDWKCDLDWHVRHCKPIYQFHGLYGEKNLSPGFNFRFARHFVQN
                                                      TM-2
Human GTNYRHLFKVFGIRFDILVDGKAGKFDIIPTMTTIGSGIGIFGVATVLCD   350
Rat   GTNRRHLFKVFGIHFDILVDGKAGKFDIIPTMTTIGSGIGIFGVATVLCD Human LLLLHILPKRHYYKQKKFKYAEDMGPGAAERDLAATSSTLGLQENMRTS*  400
Rat   LLLLHILPKRHYYKQKKFKYAEDMGPGEGEHDPVATSSTLGLQENMRTS*
```

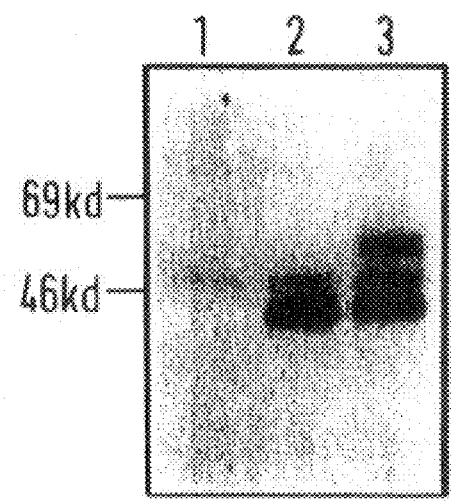
Fig. 6
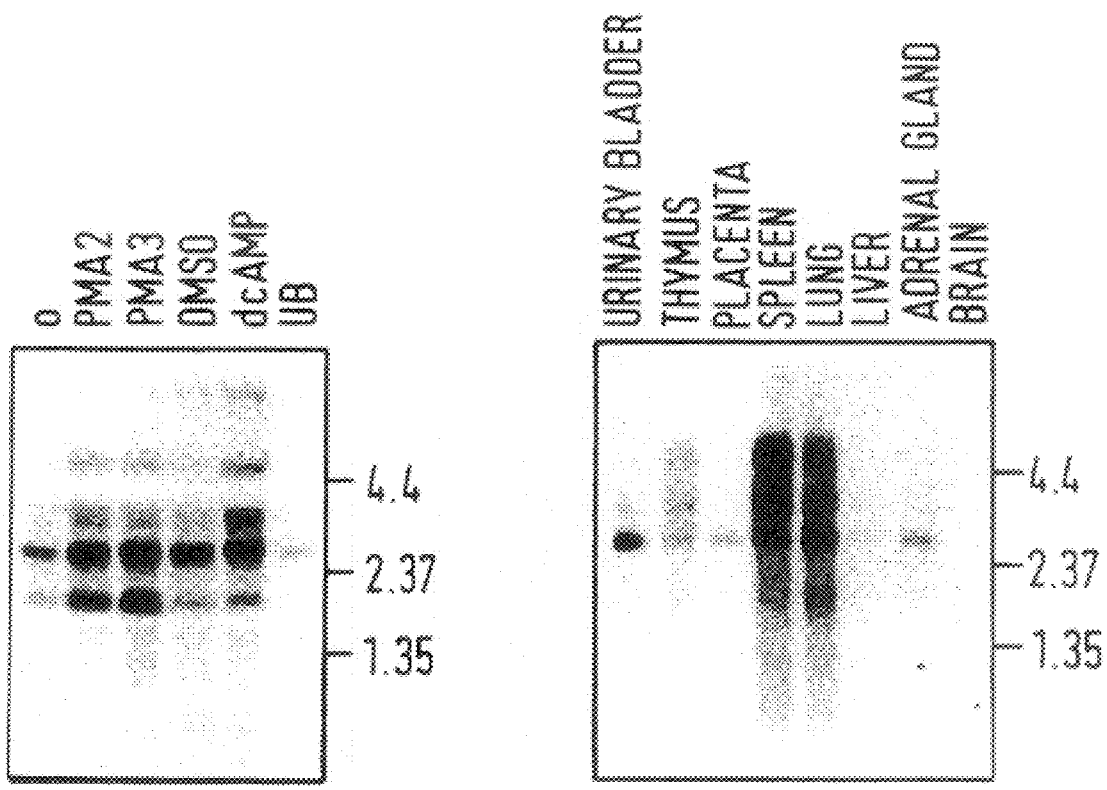
Fig. 7
Fig. 8

METHOD OF SCREENING FOR COMPOUNDS THAT BIND $P_{2X}$ RECEPTOR

This is a continuation of application Ser. No. 08/750,134, filed Jan. 22, 1997, now U.S. Pat. No. 5,985,603; which is a 371 of PCT/EP95/01968, filed May 24, 1995, the entire content of which is hereby incorporated by reference in this application.

This invention relate to the $P_{2X}$-purinoceptor, its preparation and uses.

The $P_{2X}$-purinoceptor is a ligand-gated ion channel; that is, the receptor itself forms an ion channel which opens when extracellular adenosine 5'-triphosphate (ATP) binds to the receptor. There are five other classes of neurotransmitter receptors (nicotinic acetylcholine, glutamate, glycine, $GABA_A$ and $5\text{-}HT_3$); these form a structurally related superfamily of ligand-gated ion channels (Barnard, *Trends Biochem. Sci.* 17, 368–374, (1992)). The $P_{2X}$-receptor now identifies a new family of this type of receptor. The unique structure of this receptor, the widespread distribution of this receptor throughout the body, and the numerous physiological roles this receptor may play, make it an important protein that can be used to identify new, therapeutically effective, compounds for the treatment of a number of pathological states.

In 1929 the eminent physiologist Szent-Gyorgyi described powerful cardiovascular actions of extracellular purine nucleosides (e.g. adenosine) and nucleotides (e.g. ATP) (Drury & Szent-Gyorgyi, *J. Physiol.* 68 213–237 (1929)), but it was not until 1972 that pharmacological evidence was provided to suggest the existence of distinct receptors for extracellular ATP (ie. that recognise ATP but not adenosine) (Burnstock, *Pharmacological Reviews* 21 509–581 (1972)). The seminal and subsequent work on this area by Burnstock and colleagues was largely unaccepted throughout the 1970s and early 1980s until the development of a range of relatively selective ligands and techniques for directly measuring ATP release overwhelmingly substantiated Burnstock's hypothesis (Barnard et al., *Trends Pharmacol. Sci.* 15 67–70 (1994)). In the past four or five years, unequivocal evidence for the role of ATP as a neurotransmitter has been provided for sympathetic control of blood flow to the intestine and smooth muscle tone (contractility) in genitourinary tissue such as vas deferens, bladder and ureter (Barnard et al. (loc. cit.) and Evans & Surprenant, *Brit. J. Pharmacol.* 106 242–249 (1992)). Substantial indirect evidence also exists for the role of ATP as a neurotransmitter in a number of distinct neurones in the spinal cord, autonomic ganglia and certain nuclei in the central nervous system (Bean, *Trends Pharmacol. Sci.* 15 67–70 (1992), Evans et al., *Nature* 357, 503–505 (1992) and Edwards et al., *Nature* 359 144–147 (1992)).

Purinoceptors are classified as $P_1$ (adenosine as ligand) and $P_2$ (ATP as ligand). The $P_2$ receptors are subclassified into two broad types—those that are 7-transmembrane receptors that couple to G-proteins ($P_{2Y}$, $P_{2U}$, $P_{2T}$, and perhaps $P_{2Z}$) and those that form a directly gated ion channel ($P_{2X}$). Pharmacological and/or physiological evidence for subtypes of each of these types of receptors exists. The most recent nomenclature for these receptors is shown below.

| | $P_{2X}$ | $P_{2Y}$ | $P_{2Z}$ |
|---|---|---|---|
| Type | Ligand-gated channel | G-protein coupled | Non-selective pore |
| Subtype | $P_{2X}$, $P_{2X2}$, $P_{2X3}$ | $P_{2Y}$, $P_{2Y2}$, $P_{2Y3}$ | |

Various $P_2$ receptors have previously been cloned. $P_{2Y1}$ was cloned by the Barnard/Burnstock group (Webb et al., *FEBS Lett.* 324 219–225 (1993)) based on homology with other 7-TM G-protein coupled receptors. This group used PCR technology and primers based on conserved domains of the second and sixth transmembrane regions to screen a mammalian brain cDNA library and, with final success, an embryonic chick whole-brain cDNA library.

$P_{2Y2}/P_{2U}$ was cloned by the Julius laboratory (Lustig et al., *Proc. Nat'l. Acad. Sci. USA* 90 5113–5117 (1993)) by expression cloning in the oocyte from cDNA obtained from a NG108–15 neuroblastoma cell line.

$P_{2Y3}/P_{2T}$ was also obtained by the Barnard/Burnstock group using the same probe and embnryonic brain cDNA library used to obtain the $P_{2Y1}$ receptor (Barnard et al., *Trends Pharmacol. Sci.* 15 67–70 (1994)).

However, as yet, cloning of the $P_{2X}$ receptor has remained an elusive goal. The prior cloning exercises undertaken for the other $P_2$ receptors do not provide an adequate lead to enable the $P_{2X}$ receptor to be cloned. First, all the above purinoceptors are G-protein activation of one or more second messenger systems. There are over 200 currently identified proteins which belong to this 7-TM/G-protein coupled family. Agonists at these receptors activate cascades of intracelluar transduction pathways, often involving several enzymes; the response of the cell is inherently slow (several seconds to minutes) and changes in excitability are subtle if they occur. In contrast, the $P_{2X}$ receptor is a fundamentally different type of purinoceptor that incorporates an ion channel. Activation of $P_{2X}$ receptors is rapid (milliseconds), has predominately local effects, and brings about immediate depolarisation and excitation.

Secondly, the tissue distribution of the $P_{2X}$ receptor is distinctly different from other purinoceptors, and the physiological roles differ from other purinoceptors.

One of the principal established ways to clone a receptor is based on sequence relatedness of the nucleotides that encode the amino acids of the receptor protein; it depends on there being a fairly high level of homology between a known sequence and that of the unknown receptor. This method was used to clone the $P_{2Y1}$ from (above). Several laboratories, including that of the applicants, invested significant effort in obtaining the $P_{2X}$ receptor using PCR techniques and primers based on conserved regions of various ligand-gated ion channels (ie. nicotinic ACh, GABA, glutamate, $5\text{-}HT_3$). This approach failed. With hindsight, this failure can be rationalised, as it can now, but only now, be seen that the structure of the $P_{2X}$ receptor bears no homology with any of these ligand-gated ion channels. For the same reason, approaches based on fragment hybridisation would not succeed.

However, by adopting a different approach, it has now been found possible to clone the $P_{2X}$ receptor, and it is on this achievement that the present invention is in part based.

According to a principal aspect of the present invention, there is provided a recombinant or isolated DNA molecule encoding a $P_{2X}$ receptor, wherein the receptor:

(a) has the amino sequence shown in FIG. 1, FIG. 2, FIG. 3 or FIG. 4; or (b) is substantially homologous to the sequence shown in FIG. 1, FIG. 2, FIG. 3 or FIG. 4;

or a fragment of such a DNA molecule, which fragment includes at least 15 nucleotides taken from nucleotides 1 to 813 shown in FIG. 1, the full nucleotide sequences shown in FIG. 2 and 3, or from nucleotides 1 to 1744 shown in FIG. 4.

The sequence shown in FIG. 1 is a cDNA sequence that encodes a rat vas deferens $P_{2X}$ receptor. This sequence is 1837 bases in length and encodes a protein of 399 amino acids. As was determined after the receptor was cloned, approximately one half of the protein-encoding sequence, from nucleotides 814 onwards, had been discovered previously but the function of the previously cloned sequence was not known except that it appeared to be implicated in apoptotic cell death (Owens et al., *Mol. Cell. Biol.* 11 4177–4188 (1991); the Owens et al. sequence lacks a translation initiation site and could not be made into protein. (In FIG. 1, the upstream portion of the reported sequence of Owens et al., namely PQLAHGCYPCPPHR, which is not shared with the $P_{2X}$ receptor, is shown for comparative purposes and does not form part of the invention.)

Preferably the FIG. 1 sequence fragments are taken from nucleotides 1–810. Often the FIG. 4 sequence fragments are taken from nucleotides 1–777.

The sequence shown in FIG. 2 is a cDNA sequence that encodes a rat superior cervical ganglion $P_{2X}$ receptor.

The sequence shown in FIG. 3 is a cDNA sequence that encodes a rat dorsal root ganglion $P_{2X}$ receptor.

The sequence shown in FIG. 4 is the cDNA sequence that encodes a human $P_{2X}$ receptor. The cDNA was isolated from the human urinary bladder using a rat $P_{2X}$ probe. It is 2643 bases long and encodes a 399 amino acid protein having an amino acid sequence which is highly homologous with the amino acid sequence of the rat $P_{2X}$ receptor isolated from rat vas deferens and with the rat $P_{2X}$ receptors isolated from a rat superior cervical ganglion and from a rat dorsal root ganglion. Recently we have become aware of an expressed sequence tag corresponding to residues 1745–1933 (Proc. Natl. Acad.Sci. USA 91,10645–10649 (October 1994).

Sequences which are substantially homologous to the FIG. 1, FIG. 2, FIG. 3 or FIG. 4 amino acid sequence include those which encode proteins having at least 40%, 50%, 60%, 70%, 80%, 90%, 95% or 99% homology in increasing order of preference. A protein having at least 99% homology with the amino acid sequence of FIG. 1, FIG. 2, FIG. 3 or FIG. 4 will have no more than four amino acid variations from such a sequence. Preferred substantially homologous sequences include $P_{2X}$ sequences from other species. Thus for the rat $P_{2X}$ receptor sequences a preferred substantially homologous sequence is a human $P_{2X}$ sequence. One method of determining sequence homology is disclosed in W R Pearson and D J Lipman, *Proc. Natl Acad Sci USA* 85:2444–2448 (1998).

Fragments may of course be larger than 15 nucleotides. Fragments encoding substantially the whole of the $P_{2X}$ rat receptors or human receptor may be expected to share the biological activity of the receptor, or at least some of its biological activities. Shorter fragments may be useful for encoding one or more selected domains of the receptor, or simply as probes for detecting or identifying other useful DNA sequences, including those encoding substantially homologous proteins. Fragments of at least 20, 30 or 50 nucleotides may be more frequently of use than shorter ones.

DNA molecules of the invention are useful for a number of purposes. First, and not least, the $P_{2X}$ cDNA shown in FIG. 1, in FIG. 2, in FIG. 3 and in FIG. 4 enables the relevant proteins to be expressed in living cells. This would not be possible with fragments of the cDNA. However not only are fragments of DNA within the scope of the invention, for the various purposes mentioned above, but also genomic and other sequences of DNA (including synthetic DNA and "minigenes", which include at least one, but not all, of the introns naturally present in the gene) are included within its scope. cDNA sequences encoding the rat receptor proteins or human $P_{2X}$ receptor protein may be preferred in some circumstances because such sequences are smaller than either genomic or minigene DNA and therefore more amenable to cloning manipulations. The $P_{2X}$ receptor protein can be stably expressible in chinese hamster ovary (CHO) cells, as will be described below.

Still on the subject of expression, while it would be possible to express genomic DNA in eukaryotic cells, it is much more difficult to manipulate the DNA for insertion into host cells due to the larger size that commonly results from introns. The size is particularly important for the expression of RNA; very long cRNAs—the size of whole genes—are difficult to make in sufficient quantity. On the other hand, expression from RNA is much preferred at least for the investigation of ion channel proteins, because the *Xenopus* oocyte is sufficiently large to be studied easily by electrophysiological methods.

Secondly, the cDNA sequences encode proteins that, in their predicated folding within the membrane, differ from other known proteins. This is advantageous because, based on historical precedent, this will lead to the discovery of a large family of related proteins and these may have functional roles unrelated to signalling mediated by ATP.

Thirdly, knowledge of the protein sequences encoded by rat and human $P_{2X}$ cDNA allows the development of molecular models that predict the detailed disposition within the membrane. It further allows the correctness of such models to be determined by expression of mutagenised proteins. These two approaches are advantageous because they may premit the molecular design of complementary therapeutic agents that activate or block the receptor.

Fourthly, the $P_{2X}$ cDNA sequences allow the distribution of the RNA that encodes this receptor, as well as the receptor protein itself, to be mapped in human tissues. RNA distribution can be determined by in situ hybridisation. Such hybridisation studies are disclosed in the present examples. Knowledge of a deduced amino acid sequence from cDNA allows synthetic peptides to be made that can be used to generate antibodies that selectively recognise a $P_{2X}$ receptor. Thus a $P_{2X}$ protein can be mapped by immunohistochemistry. This may suggest novel therapeutic applications for drugs that activate or block the $P_{2X}$ receptor, that can not be predicted on the basis of less sensitive current methods for localising the receptor (radioactive ligand binding).

Fifthly, rat $P_{2X}$ cDNA is advantageous because it can allow the isolation of a closely related cDNA from human tissue.

Sixthly, the isolation of the human $P_{2X}$ cDNA clone will enable a human genomic clone to be obtained. It is probable that mutations of this gene will be discovered that lead to human genetic disease. The analysis of such mutations may lead to appropriate treatments of diseases or disorders caused by such mutations.

In one aspect of the present invention rat vas deferens $P_{2X}$ receptor was cloned by a method which does not require prior inference about structure. Tissues were chosen that were believed to be rich in the RNA for the receptor of interest. A number of tissue sources were tried but they did not provide RNA that led to ATP responses in oocytes. Eventually, vas deferens was chosen. From extracted polyadenylated RNA, a cDNA library or bank that corresponds as far as possible to the DNAs in the tissue was constructed. It was not assured, either before work began or until it was satisfactorily completed, that a satisfactory cDNA library in which the rat $P_{2X}$ gene was represented could be constructed; nevertheless, this was achieved in plasmid pBKCMV.

An individual clone within the library that contains the rat vas deferens $P_{2X}$ cDNA of interest was detected by progressive fractionation of the library; at each step the fraction was tested to determine whether RNA made from it can direct the formation of the protein of interest. More specifically, RNA was transcribed in vitro from the cDNAs in the library (approximately 2 million) and the RNA ("cRNA") mixture was injected into immature Xenopus oocytes. cRNA is very susceptible to inadvertent enzymatic degradation, so all procedures were carried out under sterile conditions. The cDNA pools were made by the miniprep procedure and therefore contained large amounts of E. coli RNA; this difficulty was overcome by precipitating any RNA before the cRNA was transcribed.

Detection of the protein can in principle be done by radioactive ligand binding or by a functional response. The activation of G proteins in the Xenopus oocyte and the subsequent cellular response was used to obtain the $P_{2Y2}/P_{2U}$ receptor. In the present work, a decision was made to use the opening of the integral ion channel of the $P_{2X}$ as the response. Individual oocytes were screened two days after injection to determine whether they had made $P_{2X}$ receptor protein in their membrane. This was done by recording the current flowing across the oocyte membrane when ATP (30 $\mu$M) was applied to the outside of the oocyte; if the $P_{2X}$ receptor has been produced, a small transient current would be expected. However, testing for expression of the receptor was not straightforward, as some batches of oocytes exhibit responses to ATP because they naturally express other kinds of ATP receptor. This difficulty was overcome as follows: when an oocyte responded to ATP with the expected current this was further tested by blockade with a $P_{2X}$ receptor antagonist (suramin). The cDNA fraction that gave let to the positive response in such an oocyte was further divided, and each fraction was again tested. Such progressive fractionation led to isolation of a single clone. The insert in the plasmid was sequenced; the sequence is shown in FIG. 1. This sequence was used to design PCR primers which were used in the cloning of cDNA encoding a $P_{2X}$ receptor from a rat superior cervical ganglion (see FIG. 2). A similar procedure was then used in the cloning of cDNA encoding a $P_{2X}$ receptor from a rat dorsal root ganglion (see FIG. 3).

DNA in accordance with the invention will usually be in recombinant or isolated form and may be in the form of a vector, such as a plasmid, phagemid, cosmid or virus, and in some embodiments contains elements to direct expression of the protein, for example in a heterologous host. Non-expressible vectors are useful as cloning vectors.

Although DNA in accordance with the invention may be prepared synthetically, it is preferred that it be prepared by recombinant DNA technology. Ultimately, both techniques depend on the linkage of successive nucleotides and/or the ligation of oligo- and/or poly-nucleotides.

The invention enables, for the first time, $P_{2X}$ receptor to be prepared by recombinant DNA technology and hence free from protein with which it is naturally associated or contaminated (such as the $P_{2U}$ or, particularly, $P_{2Y}$ receptor, or other ATP receptors or binding proteins), and this in itself forms another aspect of the invention. The protein will generally be associated with a lipid bilayer, such as a cell, organelle or artificial membrane. $P_{2X}$ receptor prepared by expression of DNA in accordance with the first aspect may be glycosylated, but does not have to be. Generally speaking, receptor proteins and ion channels that are glycosylated will also function after carbohydrate removal or when expressed in cells that do not glycosylate the protein. However, there are often important quantitative differences in the function between the glycosylated and non-glycosylated protein. In the case of the rat was deferens $P_{2X}$ receptor, we believe that the native protein is glycosylated because it has a molecular weight of 62 kd when purified from the rat vas deferens, as compared to the molecular weight of 45 kd for the cloned protein. Similar results were obtained for the human $P_{2X}$ receptor (see later).

There are also several asparagine residue in the extracellular domain that are likely sites of sugar attachment.

Knowledge of the amino acid sequence of a $P_{2X}$ receptor enables the protein or peptide fragments of it to be prepared by chemical synthesis, if required. However, preparation by expression from DNA, or at least translation from RNA, will usually be preferred.

Particularly useful peptide fragments within the scope of the invention include epitopes (which may contain at least 5, 6, 7, 10, 15 or 20 amino acid residues) of the $P_{2X}$ receptor which are immunologically non-cross reactive with the RP-2 polypeptide disclosed in Owens et al., loc. cit.

A $P_{2X}$ receptor, and fragments of it, can be used to prepare specified polyclonal and monoclonal antibodies, which themselves form part of the invention. Polyclonal and monoclonal antibodies may be prepared by methods well established in the art. Hybridoma and other cells expressing monoclonal antibodies are also within the invention.

RNA encoding a $P_{2X}$ receptor, transcribable from DNA in accordance with the invention and substantially free form other RNAs, also forms part of the invention, and may be useful for a number of purposes including hybridisation studies, in vitro translation and translation in appropriate in vivo systems such as Xenopus oocytes.

The invention also relates to host cells transformed or transfected with a vector as described above. Host cells may be prokaryotic or eukaryotic and include mammalian cells (such as COS, CHO cells and human embryonic kidney cells (HEK 293 cells)), insect cells, yeasts (such as Saccharomyces cerevisiae) and bacteria (such as Escherichia coli). Host cells may only give transient expression of the receptor, as in the case of COS cells, but for preference the host cells are stably transfected with the vector. Host cells which appropriately glycosylate the receptor are preferred. A CHO cell line or any other cell line that stably expresses a $P_{2X}$ receptor can be used for electrophysiological, calcium-influx, calcium-imaging and ligand-binding studies. Host cells which do not express the receptor may still be useful as cloning hosts.

A $P_{2X}$ receptor prepared by recombinant DNA technology in accordance with the invention has a number of uses, either in situ in a membrane of the expression host or in in vitro systems. In particular the receptor can be used as a screen for compounds useful in a variety of human (or other animal) diseases and conditions, as will now be briefly described. Such compounds include those present in combinatorial libraries, and extracts containing unknown compounds (e.g. plant extracts).

Epilepsy Epilepsy results from overexcitation of distinct neurones in specific regions of the brain, in particular in the hippocampus. Functional ATP $P_{2X}$ receptors are known to be present in some hippocampal neurones. If the $P_{2X}$ receptors are expressed on inhibitory interneurons, then receptor agonists would be therapeutically useful. If the receptor is expressed on principal (pyramidal or granule) cells, then receptor antagonists will be useful. If will now be possible to determine which classes of neuron express the receptor.

Cognition Hippocampal neurones respond to ATP by activation of a $P_{2X}$ receptor; these areas are of primary importance to cognition. It is now possible to determine the cellular localisation of the $P_{2X}$ receptor with in the hippocampus; depending on this localisation, either agonists or antagonists might be effective to enhance memory.

Emesis The acute trigger for emesis is rapid contraction of smooth muscle of the upper gastrointestinal tract. Activation of ATP $P_{2X}$ receptors present on smooth muscle of the GI tract, in particular the stomach and trachea, results in strong, rapid muscle contractions. $P_{2X}$-antagonists selective for visceral smooth muscle could be useful for emesis. Furthermore, $P_{2X}$ receptors are known to be expressed in the nucleus of the tractus solitarious (Ueno et al., *J. Neurophysiol.* 68 778–785 (1992)) and may be involved in transmission from primary visceral afferents; this could be blocked by selective $P_{2X}$ antagonists.

Pain First, $P_{2X}$ receptors are expressed in dorsal horn neurones of the spinal cord. Activation of these neurones by ATP causes fast depolarizing, excitatory responses (Jahr & Jessell, *Nature* 304 730–733 (1983)); if a component of the transmission from nociceptive fibres is mediated by ATP then this could be blocked by a $P_{2X}$ antagonist. Secondly, ATP is one of the most noxious substance known when applied intradermally. This is because it activates directly the peripheral terminals of small diameter nociceptive fibres; it is known that the cell bodies in the dorsal root ganglion express $P_{2X}$ receptors. A $P_{2X}$ antagonist would be a peripherally active analgesic, and is likely to be effective in migraine.

Asthma Bronchial smooth muscles contract in response to activation of $P_{2X}$ receptors. This may occur in response to ATP released from sympathetic nerves, or from local immune cells. $P_{2X}$ antagonists may help to prevent stimulus-evoked spasms of bronchial smooth muscle and thereby reduce the frequency and/or severity of asthmatic attacks.

Peripheral vascular disease It is becoming clear that ATP and not noradrenaline is the primary vasoconstrictor neurotransmitter in small resistance arteries—those that comprise over 70% of total peripheral resistance. This has been shown for many vessels (Westfall et al., *Ann. N.Y. Acad. Sci.* 603 300–310 (1991)). A selective antagonist could be used for local collateral vasodilation.

Hypertension Hypertension that is associated with increased sympathetic tone could be treated with $P_{2X}$ receptor antagonists, because ATP is a major excitatory transmitter to many resistance vessels in several species including man (Westfall et al., loc. cit. and Martin et al., *Br. J. Pharmacol.* 102 645–650 (1991)).

Diseases of the immune system A molecule identical to part of the $P_{2X}$ receptor has been cloned from thymocytes that have been induced to die (Owens et al., loc. cit.).

The selective expression in these conditions implies that a molecule closely related to the $P_{2X}$ receptor play a role in the apoptosis that is an integral part of the selection of immunocompetent cells. The molecule described by Owens et al. (RP-2) was incomplete and could not have been translated into protein. The cloning of the $P_{2X}$ receptor will now allow the isolation of full length RP-2 clones, their heterologous expression and the determination of their functional roles.

Irritable bowel syndrome ATP is an important transmitter to the smooth muscles of the intestinal tract, particularly in the colon. It is also a transmitter between neurons in the enteric nervous system, by activating $P_{2X}$ receptors (Galligan, *Gastroenterology*, in press). Antagonists at $P_{2X}$ receptors may therefore have utility in the management of this condition.

Premature ejaculation This could be prevented by preventing stimulus-evoked contraction of vas deferens smooth muscle. $P_{2X}$ receptors are highly expressed in this tissue; antagonists at this site would prevent vas deferens contractility during sympathetic excitation.

Cystitis $P_{2X}$ receptors may be implicated in increased bladder sensitivity in patients with cystitis. Thus antagonists of such $P_{2X}$ receptors may be useful in treating cystitis.

Useful agonists and antagonists identified as described above also form an aspect of the invention.

The cloning of the $hP_{2X}$ receptor is an important aspect of the present invention. $hP_{2X}$ is the first human member of a multigene family of ionotropic purinoceptors. Its strong similarity with $P_{2X}$, isolated from rat vas deferens and with $P_{2X}$ isolated from rat superior cervical ganglion or from rat dorsal root ganglion, suggests that it is a human homolog of the rat proteins. The present inventors have found that differences between these two sequences are nearly all conservative substitutions of hydrophilic residues. Surprisingly, $hP_{2X}$ has only 41% identity with the other reported $P_{2X}$ receptor, that from rat PC12 cells (Brake et al, New structural motif for ligand-gated ion channels defined by an ionotropic ATP receptor *Nature* 371: 519–523 (1994)). The PC12 derived receptor was proposed to have a similar membrane topography and shares the conserved spacing of cysteine residues, indicated for the two smooth muscle sequences in FIG. 5.

The computed molecular weight of the $hP_{2X}$ polypeptide (45 kd) agrees with that of the in vitro translation product when made in absence of pancreatic microsomal membranes. A larger product, 60 kd, produced in presence of microsomes suggests glycosylation and supports the idea of a central extracellular domain. The predicted $hP_{2X}$ protein thus has the general features of other cloned members of this family (Valera et al, a new class of ligand-gated ion channel defined by $P_{2X}$ receptor for extracellular ATP *Nature* 371: 516–519 (1994); Brake—supra): a large, cysteine-rich extracellular central domain flanked by two transmembrane spans and short internal N- and C-termini.

The distribution of the $hP_{2X}$ mRNA was examined by northern blot analysis. Hybridisation of a principal 2.6 kb species was seen in all RNA samples tested, with the exception of brain. A smaller, 1.8 kb band, observed in spleen, and lung mRNAs could be due to a shorter 3' untranslated portion of the mRNA, as occurs for $P_{2X}$ mRNA from the rat vas deferens. The hybridisation observed in thymus, lung, spleen and liver RNA may reflect the content of smooth muscle in those organs. However, $hP_{2X}$ is likely to have roles in other cell types, as demonstrated by its presence in adrenal gland, and the hemopoertic cell line HL60. The strong induction of $hP_{2X}$ mRNA by HL60 differentiation may reflect a parallel observation in rat in which the smooth muscle form of $P_{2X}$ mRNA can be induced in immature thymocytes by dexamethasone (RP2 mRNA; Owens et al, Identification of mRNAs associated with programmed cell death in immature thymocytes *J J Mole Cell Biol* 11; 4177–4188 (1991)).

The present invention has enabled the first comprehensive pharmacological characterization of a cloned $P_{2X}$-purinoceptor to be made. The time course of the responses to ATP and the sensitivity to α, β, -methylene ATP are similar to those reported for the native $hP_{2X}$ in urinary bladder (Inue & Brading, Human, pig and guinea-pig bladder smooth muscle cells generate similar inward currents in response to purinoceptor activation Br *J Pharmacol* 103: 1840–1841 (1991)). Thus the functional properties of some native $P_{2X}$ purinoceptors can be obtained by the expression of a single molecular species. The agonist induced current recorded from ooctyes expressing the $hP_{2X}$ clone gives a direct measure of the activation of $P_{2X}$-purinoceptors in a system with low levels of endogenous ectonucleotidase activity. The agonist profile 2MeSATP≧ATP>αm β, -meATP for $hP_{2X}$ is similar to that of the cloned rat vas deferens $P_{2X}$-purinoceptor. The high potency of α, β, -meATP in whole tissue studies (α,β, -meATP>>2MeSATP≧ATP) probably reflects, its resistance to ectonucleotidases.

The concentration-effect curves for ATP, 2MeSATP and 2-chloro-ATP were superimposable, indicating that these particular substitutions at the 2' position on the adenine ring do not affect agonist binding to the $P_{2X}$-purinoceptor. The agonist activity of $AP_5A$ is likely to be because diadenosine phosphates ($AP_5A$, and $AP_6A$) released from the platelets can act as vasoactive agents through activation of $P_{2X}$-purinoceptors.

Preferred features of each aspect of the invention are as for each other aspect, mutatis mutandis.

The invention will now be illustrated by the following examples. The examples refer to the accompanying drawings, in which:

FIGS. 1A–1C show DNA and amino acid sequences of the rat vas deferens $P_{2X}$ receptor as determined in Example 2. (SEQ ID NO 4).

FIGS. 2A–2C show DNA and amino acid sequences of a rat superior cervical ganglion $P_{2X}$ receptor, as determined in Example 11. (SEQ ID NO 5).

FIGS. 3A–3C show DNA and amino acid sequences of a rat dorsal root ganglion $P_{2X}$ receptor, as determined in Example 12. (SEQ ID NO 6).

FIGS. 4A–4D show DNA and amino acid sequences of a human $P_{2X}$ receptor as determined in Example 6. (SEQ ID NO 7)

FIG. 5 shows the alignment of the predicted amino acid sequence of $hP_{2X}$ with the rat vas deferens $P_{2X}$, and in vitro translation of $hP_{2X}$ protein.

Figure 9:
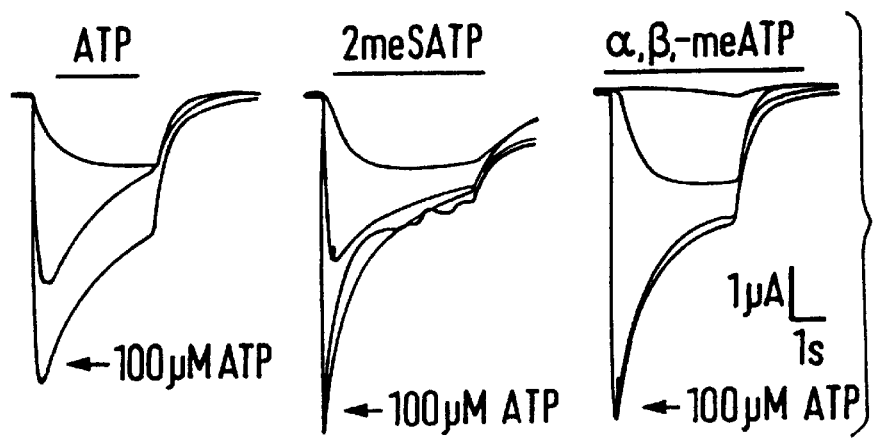

TM1 and TM2 filled boxes indicate the hydrophobic regions and boxed amino acids indicate the differences between the two sequences, o indicates conserved cysteine residues.

* Indicates potential sites of N-glycosylation.

FIG. 6 shows an SDS-PAGE analysis of $^{35}$S-methionine labelled $hP_{2X}$ protein. Lanes 1 and 2 show in vitro coupled transcription/translation of pBKCMV-$hP_{2X}$ cDNA in the absence and presence of microsomal membranes, respectively.

FIGS. 7 AND 8 show Northern analyses of the $hP_{2X}$ cDNA, wherein:

A) FIG. 7 shows Northern blot with 8 μg of total RNA from differentiated HL60 cells.

0 indicates HL60 cells without treatment;

PMA2 and PMA3 indicate respectively cells treated 2 days, and 3 days with PMA;

DMSO indicates cells treated 6 days with DMSO;

dcAMP indicates cells treated 5 days with dibutyryl cAMP;

UB indicates 100 ng of polyA$^+$ RNA from human urinary bladder; and

B) FIG. 8 shows distribution of $hP_{2X}$ in human tissues. Lanes contained 1 μg polyA$^+$ RNA except for the urinary bladder which contained 0.2 μg of polyA$^+$ RNA.

Figure 10:
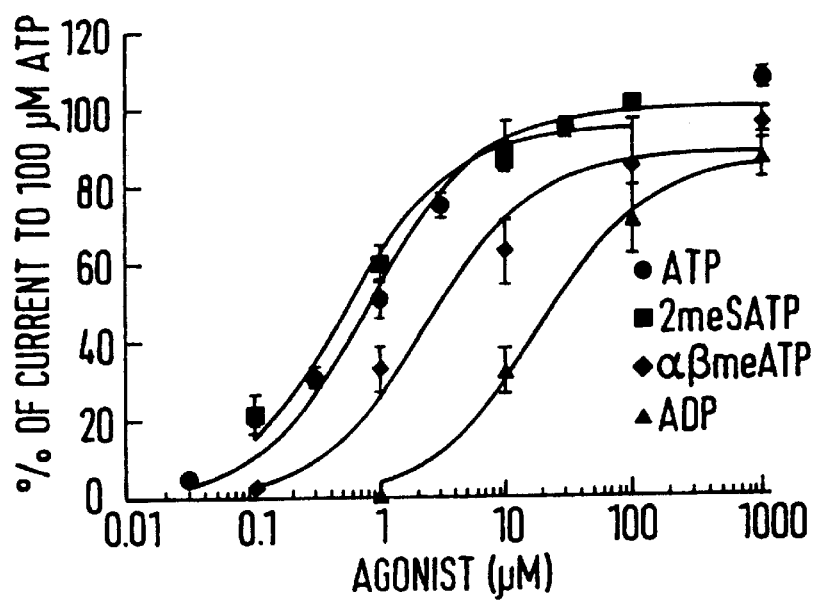
Figure 11:
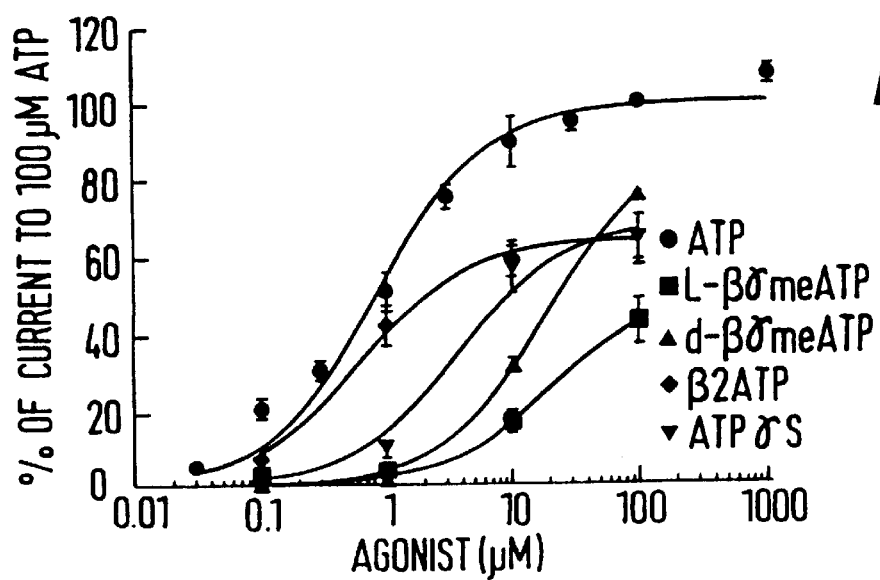

FIGS. 9, 10 and 11 show the response of oocytes expressing $hP_{2X}$ to purinoceptor agonists, wherein:

A) FIG. 9 shows traces which show inward currents evoked by ATP, 2 me SATP and α,β, me ATP (0.1, 1, and 100 μM). Records for each agonist are from separate oocytes;

B) FIG. 10 shows concentration response relationships of full $P_{2X}$-purinoceptor agonists. Data are expressed relative to the peak response to 100 μM ATP; and C) FIG. 11 shows concentration response of partial $P_{2X}$-purinoceptor agonists. Data are fitted with a Hill slope of 1 (n=4–8).

Figure 12:
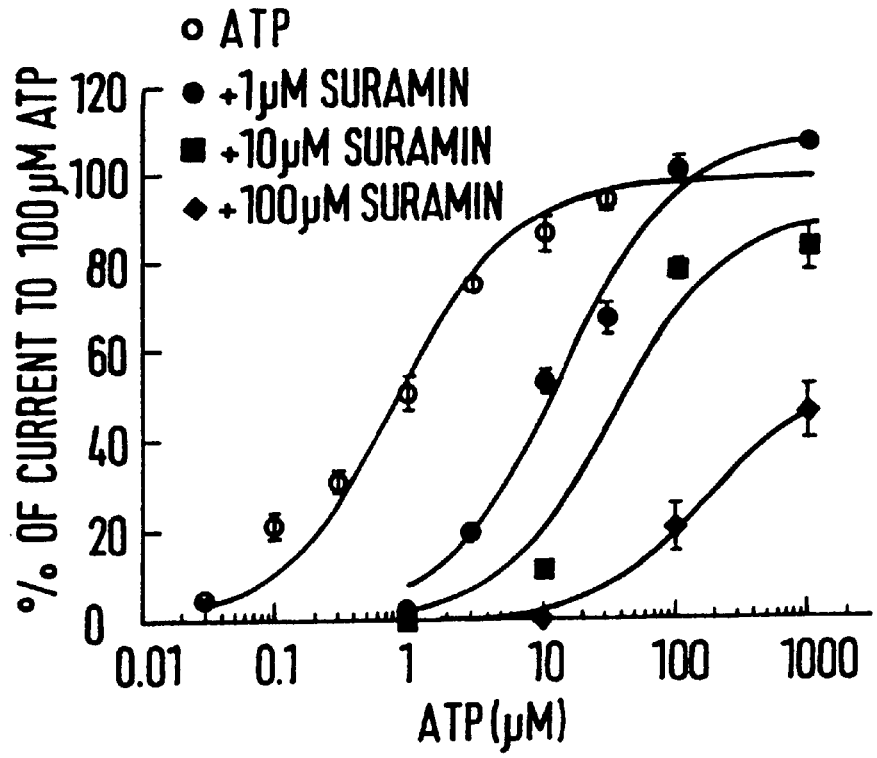
Figure 13:
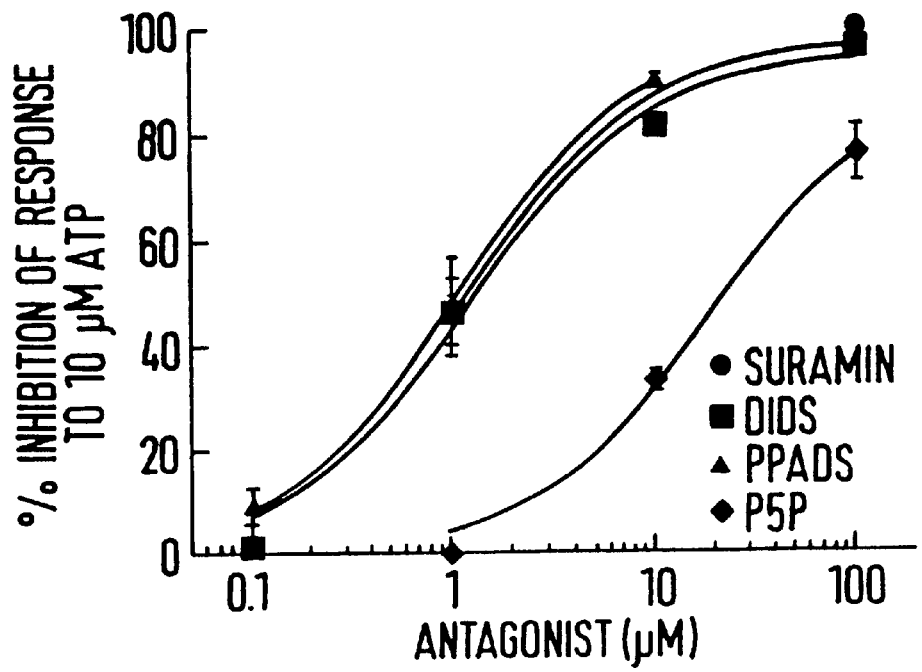
Figure 14B:
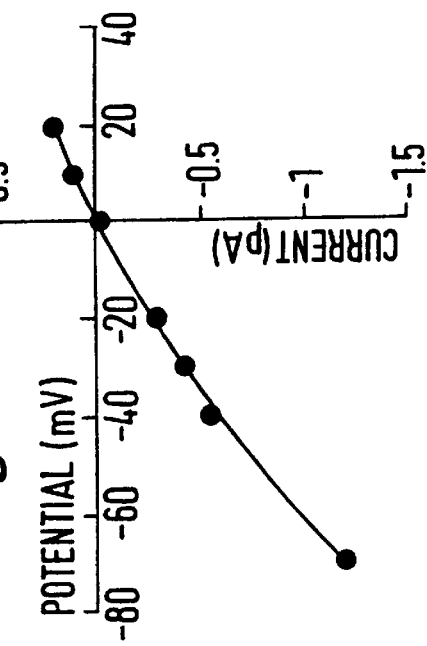
Figure 14D:
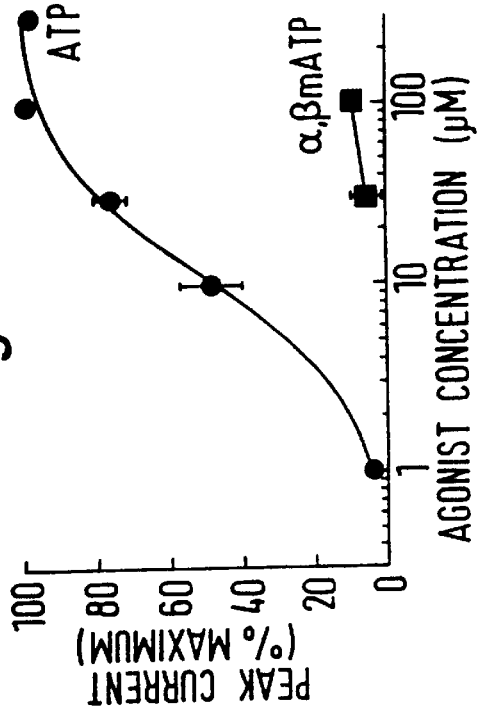
Figure 14A:
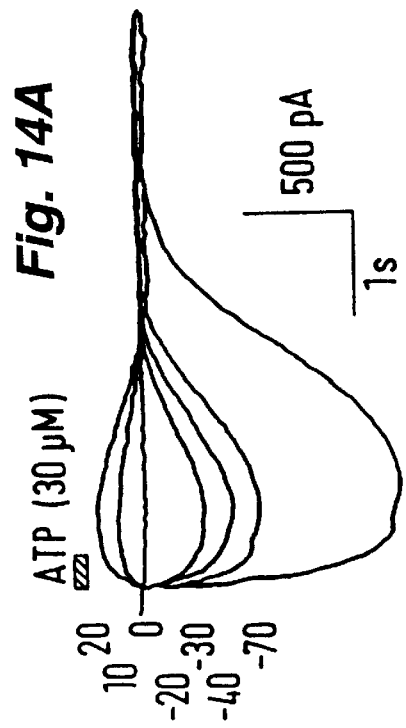
Figure 14C:
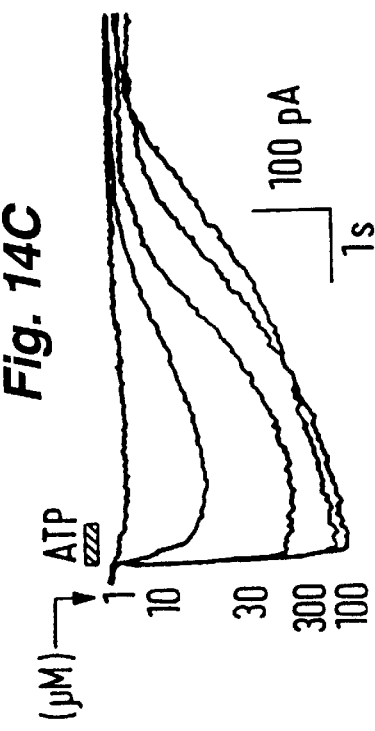

FIGS. 12 and 13 show the effects of P2-purinoceptor antagonists of $hP_{2X}$ mediated responses, wherein;

A) FIG. 12 shows concentration response curves for ATP in the presence of the P2-purinoceptor agonist suramin (1, 10 and 100 μM) (n=4 for each point); and B) FIG. 13 shows concentration dependence of suramin, DIDS PPADS and P5P in inhibiting the response to 10 μM ATP (n=4 for each point).

FIGS. 14A–14D show the results of the functional characterisation of rat superior ganglion $P_{2X}$ receptors (as encoded by clone 3, described in Example 10). These experiments provided electrical recordings from transfected HEK293 cells.

Top left: Superimposed currents evoked by ATP (30 μM) during the time are indicated by the bar. Holding potential was changed from −70 to 20 mV.

Top right: Peak current as a function of membrane potential.

Bottom left: Superimposed currents evoked by ATP, from 1 to 300 μM.

Bottom right: Concentration-response curves for ATP and αβmethylene-ATP (points are mean±s.e. mean for 5–8 experiments).

Figure 15A:
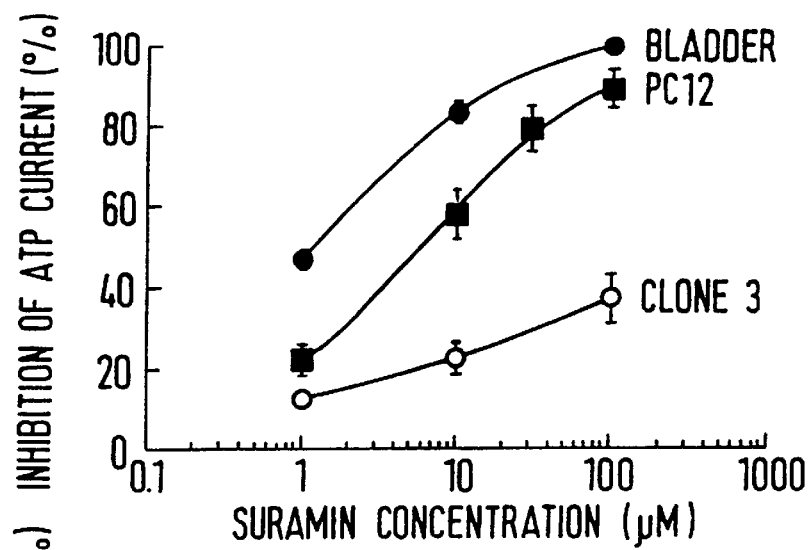
Figure 15B:
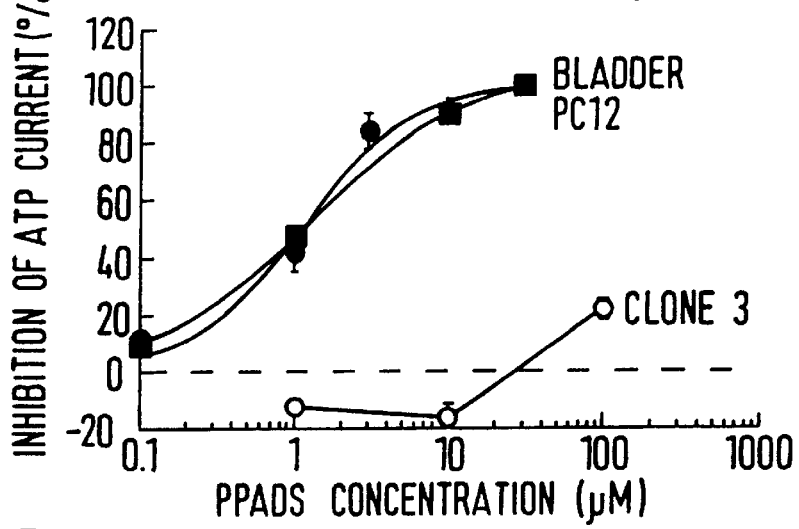
Figure 15C:
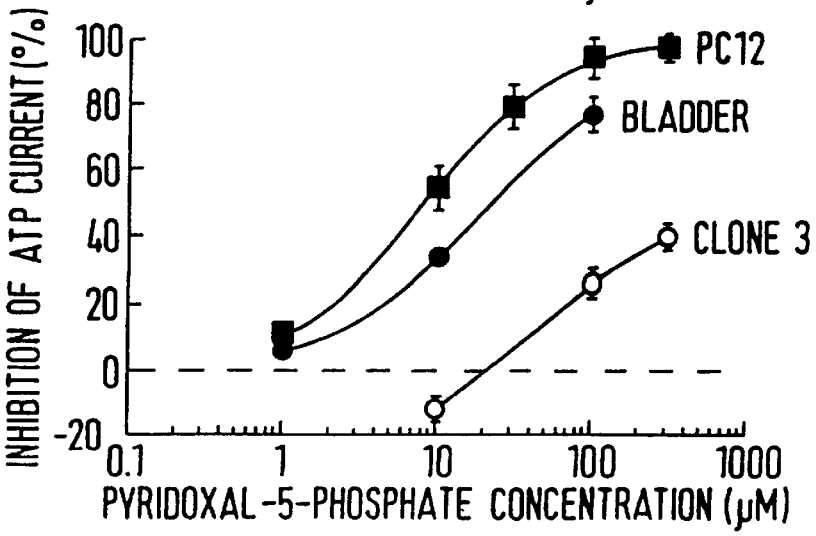

FIGS. 15A–15C show the inhibition of currents caused by various substances acting on the clone 3 form of the $P_{2X}$ receptor (as described in Example 11), compared with PC12 and human bladder forms in HEK293 cells.

Top: inhibition by suramin.

Middle: inhibition by PPADS.

Bottom: inhibition by pyridoxal 5-phosphate.

EXAMPLES (i) Rat Vas Deferens $P_{2X}$ Receptor

Example 1

Cloning of the Rat vas deferens $P_{2X}$ Receptor

Total RNA was isolated by the guanidinium isothiocyanate method (Sambrook et al., "Molecular Cloning: A Laboratory Manual" Cold Spring Harbor Laboratory Press, second edition (1989)) from vas deferens of 4 weeks old Sprague-Dawley male rats, and the poly A+ RNA was subsequently purified by oligo (dT)-cellulose. First strand cDNA primed with the sequence 5'-GAGAGAGAGAGCGGCCGCTTTTTTTTTTTTTTT-3' (SEQ ID NO 1) was synthesised with SUPERSCRIPT™ (BRL, Gaithersburg, Md., USA). After conversion of the cDNA to double stranded (Gubler & Hoffman, *Gene* 25 263–269 (1983)) EcoRI linkers were ligated to the cDNA, and the product was digested with NotI. The EcoRI-NotI cDNA of 1.3 to 9 kb was isolated by gel electrophoresis, and a unidirectional library was constructed by ligation of the cDNA to pBKCMV (Stratagene, San Diego, Calif., USA)

digested with the same enzymes. The library was electroporated into E. coli DH10B cells divided in 24 pools of $8\times10^4$ clones. The plasmid DNA from the pools was prepared by minialkaline lysis followed by LiCl precipitation (Sambrook et al., loc. cit). NotI-linearised cDNA was transcribed in vitro with T3 RNA polymerase in the presence of the cap analogue m7GpppG (Sambrook et al., loc. cit). The in vitro transcribed RNA (cRNA) was concentrated to 4 mg/ml.

Example 2

Sequencing of the Rat vas deferens $P_{2X}$ Receptor cDNA

The cDNA insert was sequenced the exonuclease method (Henikoff Meth. Enzymol. 155 156–164 (1987)). The sequence is shown in FIG. 1.

Example 3

Functional characterisation of the Rat vas deferens $P_{2X}$ Receptor cDNA in Oocytes 50 nl (200 ng) of RNA was injected into defolliculated Xenopus oocytes. After incubation for 2–6 days at 18° C., the oocytes were assayed for ATP-evoked currents by a two-electrode voltage clamp (GENECLAMP™); one electrode is to hold the voltage constant (at −100 mV), and the other is to measure the currents. A cDNA pool which showed ATP induced currents was subdivided to obtain a single clone ($P_{2X}$). Electrophysiological measurements were done at −100 mV, in a perfusion medium containing 96 mM NaCl, 2 mM KCl, 1.8 mM $CaCl_2$, 1 mM $MgCl_2$, 5 mM Hepes pH 7.6, and 5 mM sodium pyruvate. For dose-response curves and suramin inhibition, oocytes were injected with 100 ng $P_{2X}$ cRNA, and all recordings were performed at −60 mV, with $Ba^{2+}$ substituted for external $Ca^{2+}$ to prevent activation of endogenous $Ca^{2+}$-activated $Cl^-$ currents. Microelectrodes (0.5–2 MΩ) were filled with 3M KCl.

Example 4

Functional characterisation of the Rat vas deferens $P_{2X}$ Receptor cDNA in HEK 293 Cells HEK 293 cells were transfected by the lipofectin method (Felgner et al., Proc. Nat'l. Acad. Sci. USA 84 7413–7417 (1987)) with $P_{2X}$-plasmid. DNA concentration used was 1 mg/2 ml medium placed into a 35 mm petri dish containing four 11 mm diameter coverslips on which HEK cells were placed at 10,000 cells per coverslip. Cells were exposed to lipofectin/DNA for 6 h and recordings made 16–36 h later; 40–60% of cells from which recordings were made exhibited $P_{2X}$ responses. Currents were recorded from HEK 293 cells using whole-cell recording methods and the AXOPATCH™ 200 amplifier (Axon Instruments); patch pipettes (5 MΩ) contained (mM) Cs or K aspartate 140, NaCl 5, EGTA 11, HEPES 5. The external solution was (mM) NaCl 150, KCl 2, $CaCl_2$ 2, $MgCl_2$ 1, HEPES 5 and glucose 11; the pH and osmolarity of both solutions were maintained at 7.3 and 305 mosmol/l respectively. All recordings performed at room temperature. Data acquisition and analysis were performed using PCLAMP™ and AXOGRAPH™ software (Axon Instruments). Solutions for experiments examining calcium permeability of ATP currents in HEK cells contained (mM): internal solution NaCl 150, HEPES 5, $CaCl_2$ 0.5 and EGTA 5 (free calcium concentration about 5 nM); external sodium solution NaCl 150, glucose 11, histidine 5, $CaCl_2$ 2; external calcium solution $CaCl_2$ 115, glucose 11 and histidine 5. The pH and osmolarity of the solutions were 7.4 and 295 mosmol/l respectively. For single channel measurements, a GENECLAMP™ 500 amplifier and outside-out recording methods were used (Adelman et al., Neuron 9 209–216 (1992)). Wax-coated patch pipettes (5–10 MΩ) contained (mM) K-gluconate 115, HEPES 5, BAPTA 5 and $MgCl_2$ 0.5, external solution was 96 mM NaCl, 2 mM KCl, 1.8 mM $CaCl_2$, 1 mM $MgCl_2$, 5 mM Hepes pH 7.6, and 5 mM sodium pyruvate. ATP was applied by U-tube typically for 1 s; data was sampled at 5 kHz in 2 s segments beginning 300 ms prior to onset of agonist (ATP) application and filtered at 1 kHz.

Example 5

Transfection of the Rat vas deferens $P_{2X}$ Receptor cDNA into CHO and HEK293 Cells CHO cells were stably transfected by a method used for other ion channels (Claudio, Meth. Enzymol. 207 391–408 (1992)). Transfection was confirmed by a) electrophysiological recording and b) radioligand binding. ATP and other agonists (up to 30 µM) caused rapidly desensitising inward currents in 14 of 14 CHO cells stably transfected, and had no effect in 45 of 45 non-transfected cells. [$^3$H] αβmethyleneATP binding was more than 600 cpm per million transfected cells with less than 80 cpm nonspecific binding.

Stable transfection of HEK293 cells was also achieved. This was confirmed by electrophysiological recording.

(ii) Human $P_{2X}$ Receptor

The materials and methods used in the human $P_{2X}$ receptor examples are set out below:

In Vitro translation In vitro coupled transcription/translation were performed using Promega's TNT Coupled reticulocyte lysate Systems with or without 2 µl of canine pancreatic microsomal membranes (Promega). µg Circular pBKCMV-h$P_{2X}$ (0.5 ug) was transcribed with the T3 RNA polymerase as described in the system manual in a 25 µl reaction for 2 h are 30° C. Synthesized proteins (5 µl) were analysed by SDS-PAGE and autoradiography.

Differentiation of HL60 cells HL60 cells (human promyelocytes ATCC CCL240) were passaged twice weekly in RPMI-1640 supplemented with 25 mM HEPES, 2 mM Glutamax II, and 10% heat-inactivated fetal calf serum (GIBCO BRL). For each experiment $33\times10^6$ cells were resuspended at $2.5\times10^5$ cells/ml in medium containing either phorbol mystate acetate (100 nM), 1.1% DMSO, or dibutyryl cAMP (200 µM) (SIGMA) for the indicated times.

Northern blot analysis PolyA$^+$ RNAs were obtained from Clontech Laboratories Inc. (Palo Alto) except for the urinary bladder and HL60 mRNA which were prepared as described (Valera et al (1994)—supra). Samples were quantified by measuring the O.D. at 260 nm, and by staining the membrane with methylene blue. The RNA were fractionated on a 1% agarose—6% formaldehyde gel and electroblotted to a non-charged nylon membrane (BDH). Prehybridisation at 68° C. was performed for 6 hours in hybridisation buffer (50% formamide, 5X SSC, 2% blocking buffer (Boehringer Mannheim ), 0.1% laurolylsarcosine, 0.02% SDS). Hybridisation was overnight at 68° C. in fresh hybridisation buffer with a digoxigenin-UTP labelled riboprobe (100 ng/ml) corresponding to the entire h$P_{2X}$ sequence. The membrane was washed at 68° C.; twice in 2X SSC+0.1% SDS, and twice in 0.1X SSC+0.1% SDS. Chemiluminescent detection of hybridisation was carried at room temperature as follows: the membrane was rinsed 5 min in buffer B1 (0.1 M maleic acid, 0.15 M NaCl, pH 7.5), saturated for 1 hour in 1% blocking buffer (B2), incubated 30 min with anti-digoxigenin-antibody alkaline phosphatase conjugated (750 u/ml, Boehringer Mannheim) diluted 1:15000 in B2, washed in B1+0.3% tween 20 (1X 5 min, 1X 15 min, 1X 1 h), equilibrated for 5 min in buffer B3 (0.1 M Tris HCl pH 9.5, 0.1 M NaCl, 50 mM MgCl₂), incubated 45–60 sec in lumigen PPD (Boehringer Mannheim) diluted 1:100 in B3. The humid membrane was sealed in a plastic bag, incubated 15 min at 37° C., and exposed 15 to 20 min to Hyperfilm-ECL (Amersham).

$P_{2X}$ expression into oocytes Human urinary bladder $P_{2X}$ cDNA, subcloned into the pBKCMV expression vector, was linearized with NotI, and transcribed in vitro with T3 polymerase in the presence of cap analogue m7G (5')ppp(5')G. Defolliculated Xenopus oocytes (Bertrand et al, Electrophysiology of neuronal nicotinic acetylcholine receptors expressed in Xenopus oocytes following nuclear injection of genes or cDNAs Meth Neurosci 4: 174–193 (1991)) were injected with 50 ng of human $P_{2X}$ in vitro transcribed RNA, and incubated at 18° C. for 2–6 days in the ND96 solution (mM); NaCl96, KCl2, MgCl₂ 1, CaCl₂ 2, sodium pyruvate 5, HEPES 5, ph 7.6–7.5, penicillin (10 U/ml), and streptomycin (10 μg/ml).

Electrophysiology Oocytes were placed in a 1 ml chamber and superfused at 2–3 ml/min with ND96 solution with 0.1 mM BaCl₂ replacing the 2 mM CaCl₂ to prevent activation of endogenous calcium-activated chloride currents (Barish, A transient calcium-dependent chloride current in the immature Xenopus oocytes J Physiol 342: 309–325 (1983)). Currents were measured using a two-electrode voltage-clamp amplifier (Geneclamp Axon Instruments) at a holding potential of –60 mV. Microelectrodes were filled with 3 M KCl (0.5–2 MΩ). Data were collected using PClamp software (Axon Instruments). ATP and other purinoceptor agonists were applied by a U-tube perfusion system (Fenwick et al, A patch clamp study of bovine chromaffin cells and their sensitivity to acetylcholine J Physiol 331: 577–597 (1982)) placed close (200–500 μm) to the oocyte. Initial studies showed that reproducible responses (<10% variation in peak amplitude) could be obtained when ATP (at concentrations up to 1 mM) was applied to $hP_{2X}$ injected oocytes for 5 s every 10 mins. Concentration response relationships to ATP and its analogs were determined by measuring the peak amplitude of responses to a 5 s application of agonist applied at 10 min intervals. Responses to agonists were normalized in each oocyte to the peak response evoked by 100 μM ATP; 100 μM ATP was usually applied at the beginning and at the end of an experiment to determine if there was any rundown of the response. No inward current was recorded in uninjected oocytes in response to application of purinoceptor agonists at the maximal concentration used (n=3 for each agonist). Antagonists were applied both in the superfusate and together with ATP in the U-tube solution. Antagonists were superfused for 5–10 min prior to the application of ATP.

Data analysis Concentration response curves for purinoceptor agonists were fitted with a Hill slope of 1. Equi-effective concentrations i.e. concentration of agonist, giving 50% of the response to 100 μM ATP, (EEC₅₀) were determined from individual concentration response curves. For antagonists the concentration required to give 50% inhibition (IC50) of the response to 10 μM ATP (approximately 90% of peak response to ATP) were determined. Data are presented throughout as mean±SEM for a given number of oocytes.

Drugs Adenosine, adenosine 5'-monophosphate sodium salt (AMP), adenosine 5'-diphosphate sodium salt (ADP), adenosine 5'-triphosphate magnesium salt (ATP), adenosine 5'-O-(-3-thiophosphate) tetralithium salt (ATP-γ-S), uridine 5'-triphosphate sodium salt (UTP), α,β-methylene ATP lithium salt (α,β, -meATP), β,γ-methylene-D-ATP sodium salt (D-β,γ-meATP), 2'-3'-O-(4-benzoylbenzol)ATP tetraethylamonium salt (BzATP), 4,4'-diisothiocyanatostilbene 2,2'-disulphonic acid, disodium salt (DIDS) were obtained from Sigma. 2-MethylthioATP tetra sodium salt (2MeSATP) , 2-chloro-ATP tetra sodium salt, and β-γ-methylene-1-ATP (1-β-γ-meATP) were obtained from RB1. Pyridoxal 5-phosphate monohydrate (Aldrich), p1, p5-di[adenosine-5']pentaphosphate trilithium salt (AP5A) (Boehringer Mannheim), pyridoxal phosphate 6-azophenyl 2',4'-disulphonic acid (PPADS, gift of G. Lambrecht, University of Frankfurt) and suramin (Bayer) were tested. Drugs were prepared from frozen aliquots of stock solutions and diluted to give the required final concentration.

Example 6

Sequence and characteristics of $hP_{2X}$ from urinary bladder

Isolation of human $P_{2X}$ cDNA Human urinary bladder tissue was obtained from a cystectomy for a bladder tumor. The patient showed no symptoms of bladder instability or urodynamic abnormalities. Only those portions, surrounding the tumor, which appeared macroscopically normal (Palea et al—supra) were used. Total RNA was isolated by guanidinium isothiocyanate and poly A⁺ RNA was purified as described (Valera et al (1994)—supra). Preparation of a cDNA library in λgt10, random primer labelling of a rat smooth muscle $P_{2X}$ probe (Valera et al (1994)—supra), low stringency hybridisation screening and lambda phage DNA isolation were all done by standard protocols (Sambrook et al, Molecular Cloning, A Laboratory Manual, 2nd edn., Cold Spring Harbor Laboratory Press, New York (1989)). Several independent phage isolates were examined and the cDNA insert from one was chosen for subcloning into Eco RI-Not I digested pBKCMV. This 2677 bp $hP_{2X}$ cDNA was sequenced as described (Valera et al (1994)—supra).

The 2677 bp cDNA, $hP_{2X}$, contained a single long open reading frame which corresponds to a protein of 399 amino acids (FIG. 4). This amino acid sequence is highly homologous with that of the $P_{2X}$ receptor, isolated from rat vas deferens (89% identity). There are two regions of hydrophobicity near either end of the protein which are sufficiently long to traverse the membrane but there is no hydrophobic N-terminal leader sequence. All five potential sites for glycosylation and all ten cysteine residues in the central section of the protein are conserved. In vitro translation of $hP_{2X}$ RNA in the presence of microsomes produced a 60 kD product, whereas translation in the absence of microsomes produced the 45 kD peptide (FIG. 6). 45 kD is the computed molecular weight, suggesting that the additional 15 kD results from glycosylation.

Some human urinary bladder $P_{2X}$ cDNA was used to transfect HEK293 cells. Stable transfection was confirmed by electrophysiological recording.

Example 7

Distribution of human urinary bladder $P_{2X}$ mRNA

The distribution of the human urinary bladder $P_{2X}$ mRNA was examined by northern analysis. A single 2.6 kb mRNA species was observed in bladder, placenta, liver and adrenal gland (FIG. 8). In thymus, spleen, and lung samples, the 2.6 kb band plus additional higher molecular weight RNAs of 3.6 and 4.2 kb were seen. A smaller additional RNA species of 1.8 kb was observed in spleen and lung. No hybridisation was detected with brain mRNA.

Example 8

Induction of $hP_{2X}$ mRNA in HL60 cells

A portion of the 3'-untranslated region had been previously deposited in the database (HSGS01701) as an expressed sequence tag for the differentiation of the human promyelocytic cell line, HL60 (Okubo unpublished). We examined the induction of $hP_{2X}$ mRNA in HL60 cells by Northern blot analysis (FIG. 7). HL60 cells can be differentiated into distinct lineages, depending on the inductant (Koeffler, Induction of Differentiation of Human Acute Myelogenous Leukemia Cells: Therapeutic Implications *Blood* 62: 709–721 (1983)). Induction of macrophage-like characteristics with phorbol diesters or granulocytic differentiation with DMSO or dibutryl cAMP, each produced an increase in $P_{2X}$ mRNA (FIG. 7, lane 6), HL60 RNA (lane 1–5) showed hybridisation of two bands (1.8 and 2.6 kb) and both of these were inducible. This contrasts with the bladder, where Northern analysis showed only a single RNA species (2.6 kb) (FIG. 7, lane 6).

Example 9
Pharmacological characterization of $hP_{2X}$

Application of ATP (30 nM-1 mM) to oocytes injected with $hP_{2X}$ receptor RNA evoked inward currents (FIGS. 9, 10 and 11). Responses to low concentrations of ATP (30–300 nM) developed over 3–5 s. Higher concentrations of ATP (1 μM) evoked responses which peaked within 1–1.5 s and then declined during the continued application of ATP (40–60% of the peak amplitude after 5 s). The current returned to control values on washout of ATP. The peak amplitude of the inward current evoked by ATP was concentration-dependent (FIGS. 9, 10 and 11) and could be fitted by a curve with a Hill slope of 1 with a $EC_{50}$ of 0.82 μM. When ATP (100 μM) was applied for 5 s every 10 min, reproducible inward currents were recorded. This is in contrast to the responses of the $P_{2X}$ receptor clone from rat vas deferens where a second application of ATP (>1 μM) applied 10 mins after the first, evoked an inward current that was ~50% of the initial peak amplitude.

Concentration-response curves were constructed for a number of other P2 purinoceptor agonists (FIGS. 9, 10 and 11). 2meSATP, 2-chloro-ATP, α,β-meATP and ADP were full agonists. BzATP, $AP_5A$ and ATP-γ-S produced maximal responses of about 65% of the maximal ATP response. The maximal responses to d and 1-β,γ-meATP were not determined. Adenosine, AMP and UTP (100 μM) evoked small inward currents (2.3±1.5, 6.08±2, and 3.7±1.8% of the response to 100 μM ATP respectively). The $EEC_{50}$ values and relative potencies of purinoceptor analogs are summarised in Table 1 below.

TABLE 1

| agonist | EEC50 (μM) | relative potency |
|---|---|---|
| ATP | 0.82 | 1 |
| 2MeSATP | 0.6 ± 0.1 | 1.36 |
| 2chloroATP | 0.76 ± 0.1 | 1.08 |
| AP5A | 2 ± 0.2 | 0.41 |
| α,β-meATP | 3.6 ± 1.6 | 0.23 |
| BzATP | 4.2 ± 2.2 | 0.20 |
| ATP-γ-S | 10.6 ± 3.8 | 0.077 |
| d,β,γ-meATP | 24.1 ± 1.6 | 0.034 |
| ADP | 34.3 ± 16 | 0.024 |

EEC50: Equi-effective concentrations producing an inward current equivalent to 50% of the peak response to 100 μM ATP. EECSO taken from individual fitted concentration response curves with a Hill slope of 1. EEC50 for ATP from mean data from all experiments. (n = 3–4).

Example 10
Antagonist studies

The P2-purinoceptor antagonist suramin (1–100 μM) shifted the concentration-response curve for ATP to the right. At 1 μM suramin the shift was almost parallel. The dissociation equilibrium constant ($K_B$) estimated from $K_B=1/(DR-1)$ where DR is the dose ratio was 130 nM. With higher concentrations of suramin the inhibition did not appear to be competitive. Under the present experimental conditions this $K_B$ estimate is higher than those reported previously for suramin (pA2 5.9, Trezise et al, *Br J Pharmacol* 112: 282–288 (1994)) $pK_B$ 5.2, von Kugelgen et al, Interaction of adenine nucleotides, UTP and suramin in mouse vas deferens: suramin-sensitive and suramin-insensitive components in the contractile effect of ATP *Naunyn Schmiedeberg's Arch Pharmacol* 342: 198–205 (1990)). The antagonism by suramin was fully reversed after 10 mins wash and indicates that the non-competitive antagonism at high concentrations is not due to irreversible binding of the antagonist to the receptor.

The putative $P_{2X}$ purinoceptor antagonists PPADS, DIDS and pyridoxal 5 phosphate (Ziganshin et al, Selective antagonism by PPADS at $P_{2X}$ purinoceptors in rabbit isolated blood vessels *Br J Pharmacol* 111: 923–929 (1994), Bultmann & Starke, Blockade by 4,4'-diisothiocyanatostilben-2,2'-disulphonate (DIDS) of $P_{2X}$ purinoceptors in rat vas deferens *Br J Pharmacol* 112: 690–694 (1994), Trezise et al, *Eur J Pharmacol* 259: 295–300 (1994)) inhibited inward currents evoked by 10 μM ATP (approximately $EC_{90}$ concentration) in a concentration dependent manner (FIGS. 12 and 13). Suramin PPADS and DIDS were equally effective in inhibiting ATP evoked currents ($IC_{50}$ ~1 μM). The IC 50 for P5P was ~20 μM. PPADS and P5P antagonism was readily reversible on washout. In contrast, inhibitory effects of DIDS (100 μM) were very slow to reverse on washout.

(iii) Rat Superior Cervical Ganglion $P_{2X}$ Receptor

Example 11
Isolation and functional expression of a cDNA encoding a $P_{2X}$ receptor from rat superior cervical ganglion (referred to herein as clone 3)

A 440 bp fragment was amplified by polymerase chain-reaction (PCR) from rat testis cDNA, using degenerate primers based on conserved nucleotide sequences within the rat vas deferens $P_{2X}$ receptor cDNA and on the sequence of PC12 cDNA (Ehrlich H A (ed) *PCR Technology* MacMillan, Basingstoke (1989)). The primers used are given below:

```
Sense                                       (SEQ ID NO 2)
5'T G T/C G A A/G A/G T I T T/C I G G/C I T G G T
G T/C C C 3'

Antisense                                   (SEQ ID NO 3)
5'G C A/G A A T/C C T A/G A A A/G T T A/G T/A A
I C C 3'
```

(wherein I=Inosine and "T/C" indicates that either T or C is present at the position indicated (this applies mutatis mutandis to the other alternatives given).

The cloned PCR fragment was labelled and used as a hybridization probe for screening a rat testis cDNA bank in λZAP. One recombinant phage was positive, and its insert was excised and transferred to a plasmid (#432). This cDNA was 1500 bp with a single EcoR1 site (at position 1000, still in the open reading frame). The 5' end of the cDNA was too short to encode the entire N terminus.

Internal primers specific to the new sequence were made and the tissue distribution was tested by PCR. The candidate was present in mRNA prepared from phaeochromocytoma (PC12) cells, intestine and superior cervical ganglion (scg). The hybridization probe was therefore used to screen a rat scg cDNA bank in λgt10. From 30 initial positives, 20 pure phage DNA stocks were prepared; 19 were various portions of the candidate sequence, and the insert from one was transferred to plasmid (p457) and sequenced. The insert appeared to be a full length cDNA; it has a single open reading frame of 388 amino acids (FIG. 2). The insert from p457 was subcloned into pcDNA3 (p464) and used to transfect human embryonic kidney (HEK293) cells.

The functional characterisation of the clone illustrated in FIG. 2 (referred to herein as clone 3) was carried out by electrical recordings from transfected HEK293 cells and from oocytes injected with the in vitro transcribed RNA, as described in Example 4 for the rat vas deferens $P_{2X}$ receptor. Table A summarizes the main properties of clone 3 as compared to those of rat vas/human bladder cDNA clone, and the PC12 cDNA clone (provided by David Julius and Tony Brake of the University of California at San Francisco).

TABLE A

Functional Properties of 3 cloned $P_{2X}$ Receptors

|  | bladder | clone 3 | PC12 |
|---|---|---|---|
| kinetics |  |  |  |
| desensitization | very strong | very little | very little |
| rundown | profound | very little | very little |
| ionic permeability |  |  |  |
| monovalent | no differences | no differences | no differences |
| divalent (Ca$^{++}$) | high permeability | high permeability | high permeability |
| Ca$^{++}$ block | none | intermediate | very strong |
| agonist profile |  |  |  |
| ATP | 0.7 μM | 11 μM | 8 μM |
| α,β-meATP | 3 μM | >>100 mM | >>100 μM |
| antagonist profile |  |  |  |
| suramin | 1 μM | <40% block | 6 μM |
| PPADS | 1 μM | <30% block | 1 μM |
| P-5-P | 6 μM | <40% block | 6 μM |
| DIDS | 1 μM |  | >100 μM |

The main functional properties of clone 3 are as follows. (a) The currents evoked by ATP show little or no decline during applications of several seconds; that is, there is little desensitisation (FIG. 14). (b) The relative permeabilities of the ionic pore to sodium, potassium, cesium, tetraethylammonium and to calcium are not different to those observed for the rat vas deferens/human bladder or the PC12 forms of the receptor. (c) Extracellular calcium (30 mM) inhibits the inward current through the $P_{2X}$ receptor channel of the PC12 form whereas it does not block current through the rat vas deferens/human bladder form; clone 3 is intermediate in sensitivity. (d) The effectiveness of agonists that are structurally related to ATP is the same as that found for the PC12 form; most notably, αβmethylene ATP has little or no agonist action (FIG. 14). (e) Currents activated by ATP at the clone 3 receptor were much less sensitive to antagonism by suramin., pyridoxal 5'-phosphate and pyridoxal-6-azophenyl-2',4'-disulphonic acid (PPADS) than were similar current mediated by the other two forms (rat vas deferens/human bladder; PC12) (FIG. 15).

(iv) Rat Dorsal Root Ganglion $P_{2X}$ Receptor

Example 12

Isolation of a cDNA encoding a $P_{2X}$ receptor from a rat dorsal root ganglion By using PCR with the same primers as used in Example 11 above, but using different cDNA sources, further $P_{2X}$ family members can be found.

Using this method, rat dorsal root ganglion $P_{2X}$ receptor cDNA was isolated. FIG. 1B shows the cDNA sequence of this clone (referred to herein as clone 6), together with the putative amino acid sequence. The portions underlined in this figure correspond to the PCR primers initially used.

A similar procedure to that described in Example 11 was then used to isolate the full length cDNA.

What is claimed is:

1. A preparation of $P_{2X}$ receptor wherein the receptor has the amino sequence shown in SEQ ID NO:5, SEQ ID NO:7, SEQ ID NO:9 or SEQ ID NO:11 which is free of protein with which it is naturally associated or contaminated.

2. A preparation of $P_{2X}$ receptor wherein the receptor has the amino sequence shown in SEQ ID NO:5, SEQ ID NO:7, SEQ ID NO:9 or SEQ ID NO:11 which is free of $P_{2Y}$ receptor.

3. A $P_{2X}$ receptor wherein the receptor has the amino sequence shown in SEQ ID NO:5, SEQ ID NO:7, SEQ ID NO:9 or SEQ ID NO:11 prepared by recombinant DNA technology wherein said receptor is free of protein with which it is naturally associated or contaminated.

4. A method of screening for an agonist or antagonist compound of a $P_{2X}$ receptor wherein the receptor has the amino sequence shown in SEQ ID NO:5, SEQ ID NO:7, SEQ ID NO:9 or SEQ ID NO:11 which comprises a measurement of the activity of a preparation of $P_{2X}$ receptor as claimed in any one of claims 1–3, in the presence and absence of said compound, an increase in activity indicating an agonist compound and a decrease in activity indicating an antagonist compound.

5. A method of screening for an agonist compound of a $P_{2X}$ receptor wherein the receptor has the amino sequence shown in SEQ ID NO:5, SEQ ID NO:7, SEQ ID NO:9 or SEQ ID NO:11 which comprises the measurement of enhancement of activity of a preparation of $P_{2X}$ receptor as claimed in any one of claims 1–3, compared with the activity in the absence of said compound.

6. A method of screening for an antagonist compound of a $P_{2X}$ receptor wherein the receptor has the amino sequence shown in SEQ ID NO:5, SEQ ID NO:7, SEQ ID NO:9 or SEQ ID NO:11 which comprises the measurement of inhibition of activity of a preparation of $P_{2X}$ receptor as claimed in any one of claims 1–3, compared with the activity in the absence of said compound.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

GAGAGAGAGA GCGGCCGCTT TTTTTTTTTT TTT      33

(2) INFORMATION FOR SEQ ID NO: 2:

```
        (i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 2:

TGNGANNTNT NNGNNTGGTG NCC                                             23

(2) INFORMATION FOR SEQ ID NO: 3:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 3:

GCNAANCTNA ANTTNNANCC                                                 20

(2) INFORMATION FOR SEQ ID NO: 4:

(i) SEQUENCE CHARACTERISTICS:
            (A) LENGTH: 1837 base pairs
            (B) TYPE: nucleic acid
            (C) STRANDEDNESS: single
            (D) TOPOLOGY: linear (ii) MOLECULE TYPE: cDNA (vii) IMMEDIATE SOURCE:
            (B) CLONE: rat P2x from vas deferens (xi) SEQUENCE DESCRIPTION: SEQ ID NO: 4:
```

```
GCCAAAAGCT GTTCTGATCA CCCAGGGTTT TCCTCCCAA CCCAGACCCC ACCATCGAAC       60

CTCCAACTCT GGTCCCACCT AGCCTGCTCT GTCCTTAAGG GGCCGGGAAG CCCCAGTCAC     120

TCCACTGCTA TTGTAGATGC AGATGGTGGC CTGCCCTTGA CCATAGAGGC CGTGTGGGGT     180

GTTCATCTCT GAGCCCCTTC TGGCCCACC ATG GCT CGG CGG CTG CAA GAT GAG      233
                                 Met Ala Arg Arg Leu Gln Asp Glu
                                   1               5

CTG TCA GCC TTC TTC TTT GAA TAT GAC ACT CCC CGG ATG GTG CTG GTA      281
Leu Ser Ala Phe Phe Phe Glu Tyr Asp Thr Pro Arg Met Val Leu Val
     10              15                  20

CGA AAC AAG AAG GTG GGA GTC ATT TTC CGT CTG ATC CAG TTG GTG GTT      329
Arg Asn Lys Lys Val Gly Val Ile Phe Arg Leu Ile Gln Leu Val Val
 25              30                  35                  40

CTG GTC TAC GTC ATT GGG TGG GTG TTT GTC TAT GAA AAA GGA TAC CAG      377
Leu Val Tyr Val Ile Gly Trp Val Phe Val Tyr Glu Lys Gly Tyr Gln
                 45                  50                  55

ACC TCA AGT GAC CTC ATC AGC AGT GTG TCC GTG AAG CTC AAG GGC TTG      425
Thr Ser Ser Asp Leu Ile Ser Ser Val Ser Val Lys Leu Lys Gly Leu
                 60                  65                  70

GCT GTG ACC CAG CTC CAG GGC CTG GGA CCC CAG GTC TGG GAC GTG GCT      473
Ala Val Thr Gln Leu Gln Gly Leu Gly Pro Gln Val Trp Asp Val Ala
             75                  80                  85

GAC TAT GTC TTC CCA GCA CAC GGG GAC AGC TCC TTT GTA GTT ATG ACC      521
Asp Tyr Val Phe Pro Ala His Gly Asp Ser Ser Phe Val Val Met Thr
             90                  95                 100

AAC TTC ATC GTG ACC CCT CAG CAG ACT CAA GGC CAT TGT GCA GAG AAC      569
Asn Phe Ile Val Thr Pro Gln Gln Thr Gln Gly His Cys Ala Glu Asn
```

-continued

| | | |
|---|---|---|
| CCA GAA GGT GGC ATA TGC CAG GAT GAC AGT GGC TGC ACT CCA GGA AAA<br>Pro Glu Gly Gly Ile Cys Gln Asp Asp Ser Gly Cys Thr Pro Gly Lys<br>                               125                           130                         135 | 617 |

```
                105                     110                     115                     120
CCA GAA GGT GGC ATA TGC CAG GAT GAC AGT GGC TGC ACT CCA GGA AAA                              617
Pro Glu Gly Gly Ile Cys Gln Asp Asp Ser Gly Cys Thr Pro Gly Lys
                125                     130                     135

GCA GAA AGG AAA GCC CAA GGT ATT CGC ACA GGC AAC TGT GTG CCC TTC                              665
Ala Glu Arg Lys Ala Gln Gly Ile Arg Thr Gly Asn Cys Val Pro Phe
            140                     145                     150

AAT GGC ACT GTG AAG ACA TGT GAG ATC TTT GGT TGG TGT CCT GTA GAG                              713
Asn Gly Thr Val Lys Thr Cys Glu Ile Phe Gly Trp Cys Pro Val Glu
        155                     160                     165

GTG GAT GAC AAG ATC CCA AGC CCT GCT CTT CTT CGT GAG GCT GAG AAC                              761
Val Asp Asp Lys Ile Pro Ser Pro Ala Leu Leu Arg Glu Ala Glu Asn
    170                     175                     180

TTC ACC CTC TTC ATC AAA AAC AGC ATC AGC TTT CCA CGC TTC AAG GTC                              809
Phe Thr Leu Phe Ile Lys Asn Ser Ile Ser Phe Pro Arg Phe Lys Val
185                     190                     195                     200

AAC AGG CGC AAC CTG GTA GAG GAG GTG AAC GGC ACC TAC ATG AAG AAG                              857
Asn Arg Arg Asn Leu Val Glu Glu Val Asn Gly Thr Tyr Met Lys Lys
                205                     210                     215

TGC CTC TAT CAC AAG ATT CAA CAC CCC CTG TGC CCA GTC TTC AAC CTT                              905
Cys Leu Tyr His Lys Ile Gln His Pro Leu Cys Pro Val Phe Asn Leu
            220                     225                     230

GGC TAT GTG GTG CGA GAG TCA GGC CAG GAC TTC CGC AGC CTT GCT GAG                              953
Gly Tyr Val Val Arg Glu Ser Gly Gln Asp Phe Arg Ser Leu Ala Glu
        235                     240                     245

AAG GGT GGG GTG GTT GGT ATC ACC ATT GAC TGG AAG TGT GAT CTG GAC                             1001
Lys Gly Gly Val Val Gly Ile Thr Ile Asp Trp Lys Cys Asp Leu Asp
    250                     255                     260

TGG CAC GTT CGG CAC TGC AAA CCC ATC TAC CAG TTC CAC GGA CTG TAT                             1049
Trp His Val Arg His Cys Lys Pro Ile Tyr Gln Phe His Gly Leu Tyr
265                     270                     275                     280

GGG GAG AAG AAC CTG TCT CCA GGC TTC AAC TTC AGA TTT GCC AGG CAT                             1097
Gly Glu Lys Asn Leu Ser Pro Gly Phe Asn Phe Arg Phe Ala Arg His
                285                     290                     295

TTC GTG CAG AAT GGG ACA AAC CGT CGT CAC CTC TTC AAG GTG TTT GGG                             1145
Phe Val Gln Asn Gly Thr Asn Arg Arg His Leu Phe Lys Val Phe Gly
            300                     305                     310

ATT CAC TTT GAT ATC CTT GTG GAT GGC AAG GCT GGG AAG TTT GAC ATC                             1193
Ile His Phe Asp Ile Leu Val Asp Gly Lys Ala Gly Lys Phe Asp Ile
        315                     320                     325

ATC CCT ACT ATG ACT ACT ATC GGT TCT GGG ATT GGC ATC TTT GGA GTG                             1241
Ile Pro Thr Met Thr Thr Ile Gly Ser Gly Ile Gly Ile Phe Gly Val
    330                     335                     340

GCC ACA GTG CTT TGT GAT CTC TTA TTG CTC CAC ATC CTG CCT AAG AGG                             1289
Ala Thr Val Leu Cys Asp Leu Leu Leu Leu His Ile Leu Pro Lys Arg
345                     350                     355                     360

CAC TAC TAC AAG CAG AAG AAG TTC AAA TAT GCC GAG GAC ATG GGG CCG                             1337
His Tyr Tyr Lys Gln Lys Lys Phe Lys Tyr Ala Glu Asp Met Gly Pro
                365                     370                     375

GGA GAG GGT GAA CAT GAC CCC GTG GCC ACC AGC TCC ACT CTG GGC CTG                             1385
Gly Glu Gly Glu His Asp Pro Val Ala Thr Ser Ser Thr Leu Gly Leu
            380                     385                     390

CAG GAG AAC ATG AGG ACC TCC TGACCTTAGT CTTGAGATCC GGACTTGACG                                1436
Gln Glu Asn Met Arg Thr Ser
        395

CAGTGTGTGG CTTCCGGCAA GGGCTGATGG CTTTGAGCCA GGGCAGAGGG CATTCCCAGA                           1496

GGCTTTCCTG CAAGGCAGAC ACCAGTGGCC CTCTGGTTCA GCATGAAGAC AGGCAAGACT                           1556

TTGGATTTCA GAGCTCTGGT TTCAGTTCCA CATGTCCCTT CCTGAGGGAT GCCTCCTCCA                           1616
```

```
GTTTTCACCA ATTTGGGTTC ATATGGCTGG GCCCCTCACA CATCTATACT CTAGCTTTGT    1676

GCTTAAGGCT CAGGCTGTCA TTGTCTTTCC CACAGCCTTA CCTGCCTAGA TTTGGGCTCT    1736

TCCACATGGT AGCCACTAGC CAGATGTGTC AGTTTGAACT TTAATTAAAA TATAATAAAA    1796

AAAAAAAAAA AAAAAAAAAA AAAAAAAAAA AAAAAAAAA A                         1837
```

(2) INFORMATION FOR SEQ ID NO: 5:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Ala Arg Arg Leu Gln Asp Glu Leu Ser Ala Phe Phe Glu Tyr
  1               5                  10                  15

Asp Thr Pro Arg Met Val Leu Val Arg Asn Lys Lys Val Gly Val Ile
                 20                  25                  30

Phe Arg Leu Ile Gln Leu Val Val Leu Val Tyr Val Ile Gly Trp Val
             35                  40                  45

Phe Val Tyr Glu Lys Gly Tyr Gln Thr Ser Ser Asp Leu Ile Ser Ser
         50                  55                  60

Val Ser Val Lys Leu Lys Gly Leu Ala Val Thr Gln Leu Gln Gly Leu
 65                  70                  75                  80

Gly Pro Gln Val Trp Asp Val Ala Asp Tyr Val Phe Pro Ala His Gly
                 85                  90                  95

Asp Ser Ser Phe Val Val Met Thr Asn Phe Ile Val Thr Pro Gln Gln
                100                 105                 110

Thr Gln Gly His Cys Ala Glu Asn Pro Glu Gly Gly Ile Cys Gln Asp
            115                 120                 125

Asp Ser Gly Cys Thr Pro Gly Lys Ala Glu Arg Lys Ala Gln Gly Ile
130                 135                 140

Arg Thr Gly Asn Cys Val Pro Phe Asn Gly Thr Val Lys Thr Cys Glu
145                 150                 155                 160

Ile Phe Gly Trp Cys Pro Val Glu Val Asp Asp Lys Ile Pro Ser Pro
                165                 170                 175

Ala Leu Leu Arg Glu Ala Glu Asn Phe Thr Leu Phe Ile Lys Asn Ser
            180                 185                 190

Ile Ser Phe Pro Arg Phe Lys Val Asn Arg Arg Asn Leu Val Glu Glu
        195                 200                 205

Val Asn Gly Thr Tyr Met Lys Lys Cys Leu Tyr His Lys Ile Gln His
210                 215                 220

Pro Leu Cys Pro Val Phe Asn Leu Gly Tyr Val Val Arg Glu Ser Gly
225                 230                 235                 240

Gln Asp Phe Arg Ser Leu Ala Glu Lys Gly Gly Val Val Gly Ile Thr
                245                 250                 255

Ile Asp Trp Lys Cys Asp Leu Asp Trp His Val Arg His Cys Lys Pro
            260                 265                 270

Ile Tyr Gln Phe His Gly Leu Tyr Gly Glu Lys Asn Leu Ser Pro Gly
        275                 280                 285

Phe Asn Phe Arg Phe Ala Arg His Phe Val Gln Asn Gly Thr Asn Arg
    290                 295                 300

Arg His Leu Phe Lys Val Phe Gly Ile His Phe Asp Ile Leu Val Asp
```

```
305                 310                 315                 320
Gly Lys Ala Gly Lys Phe Asp Ile Ile Pro Thr Met Thr Thr Ile Gly
                325                 330                 335

Ser Gly Ile Gly Ile Phe Gly Val Ala Thr Val Leu Cys Asp Leu Leu
                340                 345                 350

Leu Leu His Ile Leu Pro Lys Arg His Tyr Tyr Lys Gln Lys Lys Phe
                355                 360                 365

Lys Tyr Ala Glu Asp Met Gly Pro Gly Glu Gly His Asp Pro Val
                370                 375                 380

Ala Thr Ser Ser Thr Leu Gly Leu Gln Glu Asn Met Arg Thr Ser
385                 390                 395
```

(2) INFORMATION FOR SEQ ID NO: 6:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
CGCAGCGAGC CTGCCGGAGC TGGTGGGTGG AGCTACGACC GGGAGCCGAC GGTGGCGAGG      60

GGACCCACAG TGTCCAAGGC GCGGAGCGGT CGGCGGAGCC ATG GCG GGC TGC TGC       115
                                             Met Ala Gly Cys Cys
                                                 400

TCC GTG CTC GGG TCC TTC CTG TTC GAG TAC GAC ACG CCG CGC ATC GTG       163
Ser Val Leu Gly Ser Phe Leu Phe Glu Tyr Asp Thr Pro Arg Ile Val
405                 410                 415                 420

CTC ATC CGC AGC CGT AAA GTG GGG CTC ATG AAC CGC GCG GTG CAG CTG       211
Leu Ile Arg Ser Arg Lys Val Gly Leu Met Asn Arg Ala Val Gln Leu
                425                 430                 435

CTC ATC CTG GCT TAC GTC ATC GGG TGG GTG TTC GTG TGG GAA AAG GGC       259
Leu Ile Leu Ala Tyr Val Ile Gly Trp Val Phe Val Trp Glu Lys Gly
                440                 445                 450

TAC CAG GAA ACG GAC TCC GTG GTC AGC TCG GTG ACA ACC AAA GCC AAA       307
Tyr Gln Glu Thr Asp Ser Val Val Ser Ser Val Thr Thr Lys Ala Lys
                455                 460                 465

GGT GTG GCT GTG ACC AAC ACC TCT CAG CTT GGA TTC CGG ATC TGG GAC       355
Gly Val Ala Val Thr Asn Thr Ser Gln Leu Gly Phe Arg Ile Trp Asp
                470                 475                 480

GTG GCG GAC TAT GTG ATT CCA GCT CAG GAG GAA AAC TCC CTC TTC ATT       403
Val Ala Asp Tyr Val Ile Pro Ala Gln Glu Glu Asn Ser Leu Phe Ile
485                 490                 495                 500

ATG ACC AAC ATG ATT GTC ACC GTG AAC CAG ACA CAG AGC ACC TGT CCA       451
Met Thr Asn Met Ile Val Thr Val Asn Gln Thr Gln Ser Thr Cys Pro
                505                 510                 515

GAG ATT CCT GAT AAG ACC AGC ATT TGT AAT TCA GAC GCC GAC TGC ACT       499
Glu Ile Pro Asp Lys Thr Ser Ile Cys Asn Ser Asp Ala Asp Cys Thr
                520                 525                 530

CCT GGC TCC GTG GAC ACC CAC AGC AGT GGA GTT GCA ACT GGA AGA TGT       547
Pro Gly Ser Val Asp Thr His Ser Ser Gly Val Ala Thr Gly Arg Cys
                535                 540                 545

GTT CCT TTC AAT GAG TCT GTG AAG ACC TGT GAG GTG GCT GCA TGG TGC       595
Val Pro Phe Asn Glu Ser Val Lys Thr Cys Glu Val Ala Ala Trp Cys
                550                 555                 560

CCG GTG GAG AAC GAC GTT GGC GTG CCA ACG CCG GCT TTC TTA AAG GCT       643
Pro Val Glu Asn Asp Val Gly Val Pro Thr Pro Ala Phe Leu Lys Ala
565                 570                 575                 580
```

```
GCA GAA AAC TTC ACC CTC TTG GTA AAG AAC AAC ATC TGG TAC CCC AAG      691
Ala Glu Asn Phe Thr Leu Leu Val Lys Asn Asn Ile Trp Tyr Pro Lys
                585                 590                 595

TTT AAC TTC AGC AAG AGG AAC ATC CTC CCC AAC ATC ACC ACG TCC TAC      739
Phe Asn Phe Ser Lys Arg Asn Ile Leu Pro Asn Ile Thr Thr Ser Tyr
                600                 605                 610

CTC AAA TCG TGC ATT TAC AAT GCT CAA ACG GAT CCC TTC TGC CCC ATA      787
Leu Lys Ser Cys Ile Tyr Asn Ala Gln Thr Asp Pro Phe Cys Pro Ile
                615                 620                 625

TTC CGT CTT GGC ACA ATC GTG GGG GAC GCG GGA CAT AGC TTC CAG GAG      835
Phe Arg Leu Gly Thr Ile Val Gly Asp Ala Gly His Ser Phe Gln Glu
                630                 635                 640

ATG GCA GTT GAG GGA GGC ATC ATG GGT ATC CAG ATC AAG TGG GAC TGC      883
Met Ala Val Glu Gly Gly Ile Met Gly Ile Gln Ile Lys Trp Asp Cys
645                 650                 655                 660

AAC CTG GAT AGA GCC GCC TCC CTT TGC CTG CCC AGA TAT TCC TTC CGG      931
Asn Leu Asp Arg Ala Ala Ser Leu Cys Leu Pro Arg Tyr Ser Phe Arg
                665                 670                 675

CGC CTG GAC ACC CGG GAC CTG GAA CAC AAT GTG TCT CCT GGC TAC AAT      979
Arg Leu Asp Thr Arg Asp Leu Glu His Asn Val Ser Pro Gly Tyr Asn
                680                 685                 690

TTC AGG TTT GCC AAG TAC TAC AGG GAC CTG GCC GGC AAA GAG CAG CGC     1027
Phe Arg Phe Ala Lys Tyr Tyr Arg Asp Leu Ala Gly Lys Glu Gln Arg
                695                 700                 705

ACA CTC ACC AAG GCG TAC GGC ATC CGC TTT GAC ATC ATC GTG TTT GGA     1075
Thr Leu Thr Lys Ala Tyr Gly Ile Arg Phe Asp Ile Ile Val Phe Gly
                710                 715                 720

AAG GCT GGG AAG TTT GAC ATC ATC CCT ACC ATG ATC AAC GTT GGC TCT     1123
Lys Ala Gly Lys Phe Asp Ile Ile Pro Thr Met Ile Asn Val Gly Ser
725                 730                 735                 740

GGC TTG GCG CTC CTC GGG GTG GCG ACG GTG CTC TGT GAC GTC ATA GTC     1171
Gly Leu Ala Leu Leu Gly Val Ala Thr Val Leu Cys Asp Val Ile Val
                745                 750                 755

CTC TAC TGC ATG AAG AAG AAA TAC TAC TAC CGG GAC AAG AAA TAT AAG     1219
Leu Tyr Cys Met Lys Lys Lys Tyr Tyr Tyr Arg Asp Lys Lys Tyr Lys
                760                 765                 770

TAT GTG GAA GAC TAC GAG CAG GGT CTT TCG GGG GAG ATG AAC CAG         1264
Tyr Val Glu Asp Tyr Glu Gln Gly Leu Ser Gly Glu Met Asn Gln
                775                 780                 785

TGACGCCTAA AGTTACATTT CCACCCCGCT CAGCCCGCGA AGCAGAAAGA TGGGGAGAGA   1324

TGGCTACTGC GTCTGTCACT CTAGAGAAAG CTCCAGAGTT TCAGCTCAGT TCTCCACTCC   1384

ACAAATACTC AGGGTTGCCA AGCACATCTT GTTGGAGCCC GGCTCTTGCT CTGCTGCTCA   1444

GATGGGCTTC CAGATACAAG AATCCTCCTG CTTCTGCCTC TAGGAATGCT GGGATCAAAC   1504

ATGTCACTTG CAATGCCCAT TTCCCATGGG GAGTTTGGCA TTTTTTACAT TTTACCCTTT   1564

CCTTTTGTAT ACATCTAAGG CTGCCCTCAG ACGCAAGACG TTCTTCCACC CTATACACCC   1624

TTTTAATCTC ACTGTGTGTG GGAGGGGGGT CGTTTGCACA CGACGCACGG TGGATGTCTG   1684

GTGTGCTGTT GGCTGGGCCA CCTGTGGCTT ATACAGTGTG AGCGTATGGA GGTAGGAAGG   1744

GTCTGAGAGC AGAGACACTG CTGTGGCTTA CGGACAGGCC CAGGCTCTGT CCACGCACTT   1804

TATTTCTAAG GAAGGAGGCT CTCTCAGGTG CTGTCAGCAG GCCTGGGACA CCATTCCTCT   1864

TCCCTATAAT CAGAGAAGTT GTCCTTGTAG CAAAGGCAGG GTTAGCTTTT CCTTTTATAA   1924

GGGCTGTGTT GAAATGACCT AGGACCAAAC ATTAAAAGAA ATAATTTTTT AAAAAAAAAA   1984

AAAAAAAAAA AAA                                                      1997
```

(2) INFORMATION FOR SEQ ID NO: 7:

(i) SEQUENCE CHARACTERISTICS:
        (A) LENGTH: 388 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Ala Gly Cys Cys Ser Val Leu Gly Ser Phe Leu Phe Glu Tyr Asp
 1               5                  10                  15

Thr Pro Arg Ile Val Leu Ile Arg Ser Arg Lys Val Gly Leu Met Asn
             20                  25                  30

Arg Ala Val Gln Leu Leu Ile Leu Ala Tyr Val Ile Gly Trp Val Phe
         35                  40                  45

Val Trp Glu Lys Gly Tyr Gln Glu Thr Asp Ser Val Val Ser Ser Val
     50                  55                  60

Thr Thr Lys Ala Lys Gly Val Ala Val Thr Asn Thr Ser Gln Leu Gly
 65                  70                  75                  80

Phe Arg Ile Trp Asp Val Ala Asp Tyr Val Ile Pro Ala Gln Glu Glu
                 85                  90                  95

Asn Ser Leu Phe Ile Met Thr Asn Met Ile Val Thr Val Asn Gln Thr
            100                 105                 110

Gln Ser Thr Cys Pro Glu Ile Pro Asp Lys Thr Ser Ile Cys Asn Ser
        115                 120                 125

Asp Ala Asp Cys Thr Pro Gly Ser Val Asp Thr His Ser Ser Gly Val
130                 135                 140

Ala Thr Gly Arg Cys Val Pro Phe Asn Glu Ser Val Lys Thr Cys Glu
145                 150                 155                 160

Val Ala Ala Trp Cys Pro Val Glu Asn Asp Val Gly Val Pro Thr Pro
                165                 170                 175

Ala Phe Leu Lys Ala Ala Glu Asn Phe Thr Leu Leu Val Lys Asn Asn
            180                 185                 190

Ile Trp Tyr Pro Lys Phe Asn Phe Ser Lys Arg Asn Ile Leu Pro Asn
        195                 200                 205

Ile Thr Thr Ser Tyr Leu Lys Ser Cys Ile Tyr Asn Ala Gln Thr Asp
    210                 215                 220

Pro Phe Cys Pro Ile Phe Arg Leu Gly Thr Ile Val Gly Asp Ala Gly
225                 230                 235                 240

His Ser Phe Gln Glu Met Ala Val Glu Gly Gly Ile Met Gly Ile Gln
                245                 250                 255

Ile Lys Trp Asp Cys Asn Leu Asp Arg Ala Ala Ser Leu Cys Leu Pro
            260                 265                 270

Arg Tyr Ser Phe Arg Arg Leu Asp Thr Arg Asp Leu Glu His Asn Val
        275                 280                 285

Ser Pro Gly Tyr Asn Phe Arg Phe Ala Lys Tyr Tyr Arg Asp Leu Ala
    290                 295                 300

Gly Lys Glu Gln Arg Thr Leu Thr Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Val Gly Ser Gly Leu Ala Leu Leu Gly Val Ala Thr Val Leu
            340                 345                 350

Cys Asp Val Ile Val Leu Tyr Cys Met Lys Lys Lys Tyr Tyr Tyr Arg
```

```
                355                 360                 365
Asp Lys Lys Tyr Lys Tyr Val Glu Asp Tyr Glu Gln Gly Leu Ser Gly
    370                 375                 380

Glu Met Asn Gln
385
```

(2) INFORMATION FOR SEQ ID NO: 8:

(i) SEQUENCE CHARACTERISTICS:
        (A) LENGTH: 1753 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
CACTGGGCTA CAGTTGCCTG GCTTACAGGA ACTGGCTCTT TTCCTCAAGC CTCATTAAGC        60

AGCCCACTCC AGTTCTTGAT CTTTGTCTCC CAGTCCTGAA GTCCTTTCTC TCCTTAGGCT       120

GCATCCACAG CCCTTCTAAG TGGCTGTGAG CAGTTTCTCA GT ATG AAC TGT ATA          174
                                            Met Asn Cys Ile
                                               390

TCA GAC TTC TTC ACC TAC GAG ACT ACC AAG TCG GTG GTT GTG AAG AGC         222
Ser Asp Phe Phe Thr Tyr Glu Thr Thr Lys Ser Val Val Val Lys Ser
        395                 400                 405

TGG ACC ATT GGG ATC ATC AAC CGA GCC GTC CAG CTG CTG ATT ATC TCC         270
Trp Thr Ile Gly Ile Ile Asn Arg Ala Val Gln Leu Leu Ile Ile Ser
    410                 415                 420

TAC TTT GTG GGG TGG GTT TTC TTG CAT GAG AAG GCC TAC CAA GTG AGG         318
Tyr Phe Val Gly Trp Val Phe Leu His Glu Lys Ala Tyr Gln Val Arg
425                 430                 435                 440

GAC ACC GCC ATT GAG TCC TCA GTA GTT ACA AAG GTG AAA GGC TTC GGG         366
Asp Thr Ala Ile Glu Ser Ser Val Val Thr Lys Val Lys Gly Phe Gly
                445                 450                 455

CGC TAT GCC AAC AGA GTC ATG GAC GTG TCG GAT TAT GTG ACC CCA CCC         414
Arg Tyr Ala Asn Arg Val Met Asp Val Ser Asp Tyr Val Thr Pro Pro
            460                 465                 470

CAG GGC ACC TCT GTC TTT GTC ATC ATC ACC AAA ATG ATC GTT ACT GAA         462
Gln Gly Thr Ser Val Phe Val Ile Ile Thr Lys Met Ile Val Thr Glu
        475                 480                 485

AAT CAA ATG CAA GGA TTC TGT CCA GAG AAT GAA GAG AAG TAC CGC TGT         510
Asn Gln Met Gln Gly Phe Cys Pro Glu Asn Glu Glu Lys Tyr Arg Cys
    490                 495                 500

GTG TCT GAC AGC CAG TGT GGG CCT GAA CGC TTC CCA GGT GGG GGG ATC         558
Val Ser Asp Ser Gln Cys Gly Pro Glu Arg Phe Pro Gly Gly Gly Ile
505                 510                 515                 520

CTC ACC GGC CGC TGC GTG AAC TAC AGC TCT GTT CTC CGG ACC TGT GAG         606
Leu Thr Gly Arg Cys Val Asn Tyr Ser Ser Val Leu Arg Thr Cys Glu
                525                 530                 535

ATC CAG GGC TGG TGC CCC ACT GAG GTG GAC ACC GTG GAG ATG CCT ATC         654
Ile Gln Gly Trp Cys Pro Thr Glu Val Asp Thr Val Glu Met Pro Ile
            540                 545                 550

ATG ATG GAG GCT GAG AAC TTC ACC ATT TTC ATC AAG AAC AGC ATC CGT         702
Met Met Glu Ala Glu Asn Phe Thr Ile Phe Ile Lys Asn Ser Ile Arg
        555                 560                 565

TTC CCT CTC TTC AAC TTT GAG AAG GGA AAC CTC CTG CCT AAC CTC ACC         750
Phe Pro Leu Phe Asn Phe Glu Lys Gly Asn Leu Leu Pro Asn Leu Thr
    570                 575                 580

GAC AAG GAC ATA AAG AGG TGC CGC TTC CAC CCT GAA AAG GCC CCA TTT         798
Asp Lys Asp Ile Lys Arg Cys Arg Phe His Pro Glu Lys Ala Pro Phe
```

```
585                     590                     595                     600
TGC CCC ATC TTG AGG GTA GGG GAT GTG GTT AAG TTT GCT GGA CAG GAT          846
Cys Pro Ile Leu Arg Val Gly Asp Val Val Lys Phe Ala Gly Gln Asp
            605                     610                     615

TTT GCC AAG CTG GCC CGC ACG GGT GGC GTT CTG GGT ATT AAG ATC GGC          894
Phe Ala Lys Leu Ala Arg Thr Gly Gly Val Leu Gly Ile Lys Ile Gly
        620                     625                     630

TGG GTG TGC GAT CTA GAC AAG GCC TGG GAC CAG TGC ATC CCT AAA TAT          942
Trp Val Cys Asp Leu Asp Lys Ala Trp Asp Gln Cys Ile Pro Lys Tyr
            635                     640                     645

TCC TTC ACT CGG CTG GAT GGA GTT TCT GAG AAA AGC AGT GTT TCC CCT          990
Ser Phe Thr Arg Leu Asp Gly Val Ser Glu Lys Ser Ser Val Ser Pro
        650                     655                     660

GGC TAC AAC TTC AGG TTT GCC AAA TAC TAT AAG ATG GAG AAC GGC AGC         1038
Gly Tyr Asn Phe Arg Phe Ala Lys Tyr Tyr Lys Met Glu Asn Gly Ser
665                     670                     675                     680

GAG TAC CGC ACA CTC CTG AAG GCT TTT GGC ATC CGC TTT GAT GTG CTG         1086
Glu Tyr Arg Thr Leu Leu Lys Ala Phe Gly Ile Arg Phe Asp Val Leu
            685                     690                     695

GTA TAT GGG AAC GCT GGC AAG TTC AAC ATC ATC CCC ACC ATT ATC AGC         1134
Val Tyr Gly Asn Ala Gly Lys Phe Asn Ile Ile Pro Thr Ile Ile Ser
        700                     705                     710

TCG GTG GCG GCC TTC ACT TCT GTG GGA GTG GGC ACT GTT CTC TGT GAC         1182
Ser Val Ala Ala Phe Thr Ser Val Gly Val Gly Thr Val Leu Cys Asp
            715                     720                     725

ATC ATC CTC CTC AAT TTC CTC AAA GGG GCT GAT CAC TAC AAA GCC AGG         1230
Ile Ile Leu Leu Asn Phe Leu Lys Gly Ala Asp His Tyr Lys Ala Arg
        730                     735                     740

AAG TTT GAG GAG GTG ACT GAG ACA ACA CTG AAG GGT ACT GCG TCA ACC         1278
Lys Phe Glu Glu Val Thr Glu Thr Thr Leu Lys Gly Thr Ala Ser Thr
745                     750                     755                     760

AAC CCA GTG TTC GCC AGT GAC CAG GCC ACT GTG GAG AAG CAG TCT ACA         1326
Asn Pro Val Phe Ala Ser Asp Gln Ala Thr Val Glu Lys Gln Ser Thr
            765                     770                     775

GAC TCA GGG GCC TAT TCT ATT GGT CAC TAGGGCCTCT TCCCAGGGTT              1373
Asp Ser Gly Ala Tyr Ser Ile Gly His
        780                     785

CCATGCTCAC CCTTAGGCTG CAGAACCTGC AAACAGGCCA CTCTATCTAA GCAGTCAGGG      1433

GTGGGAGGGG GAGAAGAAGG GCTGCTATTT CTGCTGTTCA CCCCAAAGAC TAGATCCAGA      1493

TATCTAGGCC CTCACTGTTC AACAGATAGG CAATGCTTCC CACTAAGACT TGAATCTTGC      1553

CTTTACCCCT TGCATGCCTC CCACCTGCTT CCCTGGATCC CAGGACAGCA GCATCCACCC      1613

CTTTCCAAAG GATTGAGAAA ATGGTAGCTA AGGTTACACC CATAGGACCT ACCACGTACC      1673

AAGCACTTCC ACACATATTA TCCCTTTTCA CCCTTAAAAT AATCCTATAA GGTAGAAAAA      1733

AAAAAAAAAA AAAAAAAAA                                                    1753

(2) INFORMATION FOR SEQ ID NO: 9:

(i) SEQUENCE CHARACTERISTICS:
        (A) LENGTH: 397 amino acids
        (B) TYPE: amino acid
        (D) TOPOLOGY: linear (ii) MOLECULE TYPE: protein (xi) SEQUENCE DESCRIPTION: SEQ ID NO: 9:

Met Asn Cys Ile Ser Asp Phe Phe Thr Tyr Glu Thr Thr Lys Ser Val
  1               5                  10                  15
```

```
Val Val Lys Ser Trp Thr Ile Gly Ile Ile Asn Arg Ala Val Gln Leu
             20                  25                  30

Leu Ile Ile Ser Tyr Phe Val Gly Trp Val Phe Leu His Glu Lys Ala
         35                  40                  45

Tyr Gln Val Arg Asp Thr Ala Ile Glu Ser Ser Val Val Thr Lys Val
     50                  55                  60

Lys Gly Phe Gly Arg Tyr Ala Asn Arg Val Met Asp Val Ser Asp Tyr
 65                  70                  75                  80

Val Thr Pro Pro Gln Gly Thr Ser Val Phe Val Ile Ile Thr Lys Met
                 85                  90                  95

Ile Val Thr Glu Asn Gln Met Gln Gly Phe Cys Pro Glu Asn Glu Glu
                100                 105                 110

Lys Tyr Arg Cys Val Ser Asp Ser Gln Cys Gly Pro Glu Arg Phe Pro
            115                 120                 125

Gly Gly Gly Ile Leu Thr Gly Arg Cys Val Asn Tyr Ser Ser Val Leu
        130                 135                 140

Arg Thr Cys Glu Ile Gln Gly Trp Cys Pro Thr Glu Val Asp Thr Val
145                 150                 155                 160

Glu Met Pro Ile Met Met Glu Ala Glu Asn Phe Thr Ile Phe Ile Lys
                165                 170                 175

Asn Ser Ile Arg Phe Pro Leu Phe Asn Phe Glu Lys Gly Asn Leu Leu
            180                 185                 190

Pro Asn Leu Thr Asp Lys Asp Ile Lys Arg Cys Arg Phe His Pro Glu
        195                 200                 205

Lys Ala Pro Phe Cys Pro Ile Leu Arg Val Gly Asp Val Val Lys Phe
    210                 215                 220

Ala Gly Gln Asp Phe Ala Lys Leu Ala Arg Thr Gly Gly Val Leu Gly
225                 230                 235                 240

Ile Lys Ile Gly Trp Val Cys Asp Leu Asp Lys Ala Trp Asp Gln Cys
                245                 250                 255

Ile Pro Lys Tyr Ser Phe Thr Arg Leu Asp Gly Val Ser Glu Lys Ser
            260                 265                 270

Ser Val Ser Pro Gly Tyr Asn Phe Arg Phe Ala Lys Tyr Tyr Lys Met
        275                 280                 285

Glu Asn Gly Ser Glu Tyr Arg Thr Leu Leu Lys Ala Phe Gly Ile Arg
    290                 295                 300

Phe Asp Val Leu Val Tyr Gly Asn Ala Gly Lys Phe Asn Ile Ile Pro
305                 310                 315                 320

Thr Ile Ile Ser Ser Val Ala Ala Phe Thr Ser Val Gly Val Gly Thr
                325                 330                 335

Val Leu Cys Asp Ile Ile Leu Leu Asn Phe Leu Lys Gly Ala Asp His
            340                 345                 350

Tyr Lys Ala Arg Lys Phe Glu Glu Val Thr Glu Thr Thr Leu Lys Gly
        355                 360                 365

Thr Ala Ser Thr Asn Pro Val Phe Ala Ser Asp Gln Ala Thr Val Glu
    370                 375                 380

Lys Gln Ser Thr Asp Ser Gly Ala Tyr Ser Ile Gly His
385                 390                 395
```

(2) INFORMATION FOR SEQ ID NO: 10:

(i) SEQUENCE CHARACTERISTICS:
        (A) LENGTH: 2643 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO: 10:

```
GCCTCCAGCT GACCTCTGGC TCCTGTCCTC TGGCTCCACC TGCACCGCCC TGCTCTTCCT         60

AAGGGGCCAG GAAGCCCCCA GAAGCTCTAC CATCGACGTG GGTGGTGGCA CCCGGCTCAC        120

CCTGAGAGCA GAGGGCGTGC AGGGGCTCA GTTCTGAGCC CAGCCGGCCC ACC ATG           176
                                                           Met

GCA CGG CGG TTC CAG GAG GAG CTG GCC GCC TTC CTC TTC GAG TAT GAC          224
Ala Arg Arg Phe Gln Glu Glu Leu Ala Ala Phe Leu Phe Glu Tyr Asp
    400             405             410

ACC CCC CGC ATG GTG CTG GTG CGT AAT AAG AAG GTG GGC GTT ATC TTC          272
Thr Pro Arg Met Val Leu Val Arg Asn Lys Lys Val Gly Val Ile Phe
415             420             425             430

CGA CTG ATC CAG CTG GTG GTC CTG GTC TAC GTC ATC GGG TGG GTG TTT          320
Arg Leu Ile Gln Leu Val Val Leu Val Tyr Val Ile Gly Trp Val Phe
                435             440             445

CTC TAT GAG AAG GGC TAC CAG ACC TCG AGC GGC CTC ATC AGC AGT GTC          368
Leu Tyr Glu Lys Gly Tyr Gln Thr Ser Ser Gly Leu Ile Ser Ser Val
    450             455             460

TCT GTG AAA CTC AAG GGC CTG GCC GTG ACC CAG CTC CCT GGC CTC GGC          416
Ser Val Lys Leu Lys Gly Leu Ala Val Thr Gln Leu Pro Gly Leu Gly
            465             470             475

CCC CAG GTC TGG GAT GTG GCT GAC TAC GTC TTC CCA GCC CAG GGG GAC          464
Pro Gln Val Trp Asp Val Ala Asp Tyr Val Phe Pro Ala Gln Gly Asp
        480             485             490

AAC TCC TTC GTG GTC ATG ACC AAT TTC ATC GTG ACC CCG AAG CAG ACT          512
Asn Ser Phe Val Val Met Thr Asn Phe Ile Val Thr Pro Lys Gln Thr
495             500             505             510

CAA GGC TAC TGC GCA GAG CAC CCA GAA GGG GGC ATA TGC AAG GAA GAC          560
Gln Gly Tyr Cys Ala Glu His Pro Glu Gly Gly Ile Cys Lys Glu Asp
                515             520             525

AGT GGC TGT ACC CCT GGG AAG GCC AAG AGG AAG GCC CAA GGC ATC CGC          608
Ser Gly Cys Thr Pro Gly Lys Ala Lys Arg Lys Ala Gln Gly Ile Arg
            530             535             540

ACG GGC AAG TGT GTG GCC TTC AAC GAC ACT GTG AAG ACG TGT GAG ATC          656
Thr Gly Lys Cys Val Ala Phe Asn Asp Thr Val Lys Thr Cys Glu Ile
        545             550             555

TTT GGC TGG TGC CCC GTG GAG GTG GAT GAC GAC ATC CCG CGC CCT GCC          704
Phe Gly Trp Cys Pro Val Glu Val Asp Asp Asp Ile Pro Arg Pro Ala
560             565             570

CTT CTC CGA GAG GCC GAG AAC TTC ACT CTT TTC ATC AAG AAC AGC ATC          752
Leu Leu Arg Glu Ala Glu Asn Phe Thr Leu Phe Ile Lys Asn Ser Ile
575             580             585             590

AGC TTT CCA CGC TTC AAG GTC AAC AGG CGC AAC CTG GTG GAG GAG GTG          800
Ser Phe Pro Arg Phe Lys Val Asn Arg Arg Asn Leu Val Glu Glu Val
                595             600             605

AAT GCT GCC CAC ATG AAG ACC TGC CTC TTT CAC AAG ACC CTG CAC CCC          848
Asn Ala Ala His Met Lys Thr Cys Leu Phe His Lys Thr Leu His Pro
            610             615             620

CTG TGC CCA GTC TTC CAG CTT GGC TAC GTG GTG CAA GAG TCA GGC CAG          896
Leu Cys Pro Val Phe Gln Leu Gly Tyr Val Val Gln Glu Ser Gly Gln
        625             630             635

AAC TTC AGC ACC CTG GCT GAG AAG GGT GGA GTG GTT GGC ATC ACC ATC          944
Asn Phe Ser Thr Leu Ala Glu Lys Gly Gly Val Val Gly Ile Thr Ile
640             645             650

GAC TGG CAC TGT GAC CTG GAC TGG CAC GTA CGG CAC TGC AGA CCC ATC          992
Asp Trp His Cys Asp Leu Asp Trp His Val Arg His Cys Arg Pro Ile
```

-continued

```
655              660              665              670
TAT GAG TTC CAT GGG CTG TAC GAA GAG AAA AAT CTC TCC CCA GGC TTC         1040
Tyr Glu Phe His Gly Leu Tyr Glu Glu Lys Asn Leu Ser Pro Gly Phe
            675              680              685

AAC TTC AGG TTT GCC AGG CAC TTT GTG GAG AAC GGG ACC AAC TAC CGT         1088
Asn Phe Arg Phe Ala Arg His Phe Val Glu Asn Gly Thr Asn Tyr Arg
            690              695              700

CAC CTC TTC AAG GTG TTT GGG ATT CGC TTT GAC ATC CTG GTG GAC GGC         1136
His Leu Phe Lys Val Phe Gly Ile Arg Phe Asp Ile Leu Val Asp Gly
            705              710              715

AAG GCC GGG AAG TTT GAC ATC ATC CCT ACA ATG ACC ACC ATC GGC TCT         1184
Lys Ala Gly Lys Phe Asp Ile Ile Pro Thr Met Thr Thr Ile Gly Ser
            720              725              730

GGA ATT GGC ATC TTT GGG GTG GCC ACA GTT CTC TGT GAC CTG CTG CTG         1232
Gly Ile Gly Ile Phe Gly Val Ala Thr Val Leu Cys Asp Leu Leu Leu
735              740              745              750

CTT CAC ATC CTG CCT AAG AGG CAC TAC TAC AAG CAG AAG AAG TTC AAA         1280
Leu His Ile Leu Pro Lys Arg His Tyr Tyr Lys Gln Lys Lys Phe Lys
            755              760              765

TAC GCT GAG GAC ATG GGG CCA GGG GCG GCT GAG CGT GAC CTC GCA GCT         1328
Tyr Ala Glu Asp Met Gly Pro Gly Ala Ala Glu Arg Asp Leu Ala Ala
            770              775              780

ACC AGC TCC ACC CTG GGC CTG CAG GAG AAC ATG AGG ACA TCC                 1370
Thr Ser Ser Thr Leu Gly Leu Gln Glu Asn Met Arg Thr Ser
            785              790              795

TGATGCTCGG GCCCCAACTC CTGACTGGGT GCAGCGTGAG GCTTCAGCCT GGAGCCCTGG       1430

TGGGTCCCAG CCAGGGCAGA GGGGCCTCCC CAGGAAGTCT CCTACCCTCT CAGCCAGGCA       1490

GAGAGCAGTT TGCCAGAAGC TCAGGGTGCA TAGTAGGAGA GACCTGTGCA AATCTGAGCT       1550

CCGGCTCCGA CCCCACACAC CCTGAGGGAG GCCTACCCTA GCCTCAGCCG CTCCTGGTGG       1610

GGGAATGGCT GGGGGTTGGG CAGGACCCTC CCACACACCT GCACCCTAGC TTCGTGCTTC       1670

TCTCTCCGGA CTCTCATTAT CCAACCCGCT GCCTCCATTT CTCTAGATCT GTGCTCTCCG       1730

ATGTGGCAGT CAGTAACCAT AGGTGACTAA ATTAAACTAA AATAAAATAG AATGAAACAC       1790

AAAATTCAAT TCCTCGGCTG AACTAGCCAC ATTTCAACTG CTCAGTAGAT ACGTGTGGTT       1850

AGTGGCTGCC ATACTGGACA GCTCGGGGCA TTTTCACTGT CAAAGAAAGT TCTATTAGAC       1910

AGCCCTGCTT GAGCCCTGTT TCTTCCTGGC TTCGGTTTCC CTGGGAACT TATCGACAAT       1970

GCAAGCTCCT GGGCCCACCC CCAGACCTCC TGAACCAAAA GCTCCAGGGC TGGCCGTATG       2030

ATCTGTGTGG ATGGCAAACT CCCCAGGCCA TTCTGGGACC TAAGTTTAAG AAGTGCCGTC       2090

CTCGAACTTT CTGACTCTAA GCTCCTGAGC GGGAGTCAGA CTTAGCCCTG AGCCTGCACT       2150

TCCTGTTCAG GTGCAGACAC TGAACAGGGT CTCAAACACC TTCAGCATGT GTGTTGTGTG       2210

CTCACGTGCC ACACAGTGTC TCATGCACAC AACCCAGTGT ACACACCACC TACGTGCACA       2270

CAGCATCCTT CCACACTGTG TATGTGAACA GCTTGGGCCC TGCAAACACA ACCATCTACA       2330

CACATCTACA CCCCCAAGCA CACACACATG GTCCGTGCCA TGTCACCTCC ATAGGGAAAG       2390

GCTTCTCTCC AAGTGTGCCA GGCCAGGACA GCCCTCCCAG CCATGAATCC TTACTCAGCT       2450

ACCTCGGGTT GGGGTGGGAG CCCCAGCCAA ATCCTGGGCT CCCTGCCTGT GGCTCAGCCC       2510

CAGCTCCCAA GGCCTGCCTG GCTCTGTCTG AACAGAAGGT CTGGGGAAG CGAGGGGTGG        2570

AGTACAATAA AGGGAATGAG GACAAACAAA AAAAAAAAA AAAAAAAAA AAAAAAAAA          2630

AAAAAAAAAA AAA                                                         2643
```

(2) INFORMATION FOR SEQ ID NO: 11:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO: 11:

```
Met Ala Arg Arg Phe Gln Glu Leu Ala Ala Phe Leu Phe Glu Tyr
 1               5                  10                  15

Asp Thr Pro Arg Met Val Leu Val Arg Asn Lys Lys Val Gly Val Ile
                20                  25                  30

Phe Arg Leu Ile Gln Leu Val Val Leu Val Tyr Val Ile Gly Trp Val
            35                  40                  45

Phe Leu Tyr Glu Lys Gly Tyr Gln Thr Ser Ser Gly Leu Ile Ser Ser
        50                  55                  60

Val Ser Val Lys Leu Lys Gly Leu Ala Val Thr Gln Leu Pro Gly Leu
65                  70                  75                  80

Gly Pro Gln Val Trp Asp Val Ala Asp Tyr Val Phe Pro Ala Gln Gly
                85                  90                  95

Asp Asn Ser Phe Val Val Met Thr Asn Phe Ile Val Thr Pro Lys Gln
                100                 105                 110

Thr Gln Gly Tyr Cys Ala Glu His Pro Glu Gly Gly Ile Cys Lys Glu
            115                 120                 125

Asp Ser Gly Cys Thr Pro Gly Lys Ala Lys Arg Lys Ala Gln Gly Ile
        130                 135                 140

Arg Thr Gly Lys Cys Val Ala Phe Asn Asp Thr Val Lys Thr Cys Glu
145                 150                 155                 160

Ile Phe Gly Trp Cys Pro Val Glu Val Asp Asp Ile Pro Arg Pro
                165                 170                 175

Ala Leu Leu Arg Glu Ala Glu Asn Phe Thr Leu Phe Ile Lys Asn Ser
            180                 185                 190

Ile Ser Phe Pro Arg Phe Lys Val Asn Arg Arg Asn Leu Val Glu Glu
        195                 200                 205

Val Asn Ala Ala His Met Lys Thr Cys Leu Phe His Lys Thr Leu His
210                 215                 220

Pro Leu Cys Pro Val Phe Gln Leu Gly Tyr Val Val Gln Glu Ser Gly
225                 230                 235                 240

Gln Asn Phe Ser Thr Leu Ala Glu Lys Gly Gly Val Val Gly Ile Thr
                245                 250                 255

Ile Asp Trp His Cys Asp Leu Asp Trp His Val Arg His Cys Arg Pro
                260                 265                 270

Ile Tyr Glu Phe His Gly Leu Tyr Glu Glu Lys Asn Leu Ser Pro Gly
            275                 280                 285

Phe Asn Phe Arg Phe Ala Arg His Phe Val Glu Asn Gly Thr Asn Tyr
        290                 295                 300

Arg His Leu Phe Lys Val Phe Gly Ile Arg Phe Asp Ile Leu Val Asp
305                 310                 315                 320

Gly Lys Ala Gly Lys Phe Asp Ile Ile Pro Thr Met Thr Thr Ile Gly
                325                 330                 335

Ser Gly Ile Gly Ile Phe Gly Val Ala Thr Val Leu Cys Asp Leu Leu
            340                 345                 350

Leu Leu His Ile Leu Pro Lys Arg His Tyr Tyr Lys Gln Lys Lys Phe
        355                 360                 365
```

```
Lys Tyr Ala Glu Asp Met Gly Pro Gly Ala Ala Glu Arg Asp Leu Ala
    370                 375                 380

Ala Thr Ser Ser Thr Leu Gly Leu Gln Glu Asn Met Arg Thr Ser
385                 390                 395
```